(12) United States Patent
Delgado González et al.

(10) Patent No.: US 9,393,260 B2
(45) Date of Patent: Jul. 19, 2016

(54) EXOPOLYSACCHARIDE FOR THE TREATMENT AND/OR CARE OF THE SKIN, MUCOUS MEMBRANES AND/OR NAILS

(71) Applicants: Lipotec, S.A., Gavà (ES); Polymaris Biotechnology, Morlaix (FR)

(72) Inventors: Raquel Delgado González, Gavà (ES); Albert Soley Astals, Barcelona (ES); Anthony Courtois, Morlaix (FR); Bertrand Thollas, Morlaix (FR)

(73) Assignees: Lubrizol Advanced Materials, Inc., Wickliffe, OH (US); Polymaris Biotechnology, Morlaix (FR)

( * ) Notice: Subject to any disclaimer, the term of this patent is extended or adjusted under 35 U.S.C. 154(b) by 0 days.

(21) Appl. No.: 14/386,987

(22) PCT Filed: Mar. 22, 2013

(86) PCT No.: PCT/EP2013/056080
§ 371 (c)(1),
(2) Date: Sep. 22, 2014

(87) PCT Pub. No.: WO2013/139965
PCT Pub. Date: Sep. 26, 2013

(65) Prior Publication Data
US 2015/0079137 A1  Mar. 19, 2015

(30) Foreign Application Priority Data
Mar. 22, 2012  (ES) .................................. 201230432

(51) Int. Cl.
| | | |
|---|---|---|
| *A61K 31/715* | (2006.01) | |
| *A61K 8/73* | (2006.01) | |
| *A61K 9/00* | (2006.01) | |
| *A61K 9/107* | (2006.01) | |
| *A61K 9/127* | (2006.01) | |
| *A61K 8/64* | (2006.01) | |
| *A61Q 19/08* | (2006.01) | |
| *A61K 9/50* | (2006.01) | |
| *A61K 9/51* | (2006.01) | |
| *C12P 19/04* | (2006.01) | |

(52) U.S. Cl.
CPC ................. *A61K 31/715* (2013.01); *A61K 8/64* (2013.01); *A61K 8/73* (2013.01); *A61K 9/0014* (2013.01); *A61K 9/1075* (2013.01); *A61K 9/127* (2013.01); *A61K 9/50* (2013.01); *A61K 9/51* (2013.01); *A61Q 19/08* (2013.01); *A61K 9/5042* (2013.01); *A61K 9/5057* (2013.01); *A61K 9/5123* (2013.01); *A61K 2800/43* (2013.01); *A61K 2800/48* (2013.01); *A61K 2800/51* (2013.01); *A61K 2800/522* (2013.01); *A61K 2800/524* (2013.01); *A61K 2800/75* (2013.01); *C12P 19/04* (2013.01)

(58) Field of Classification Search
CPC ... A61Q 19/08; A61Q 19/007; A61K 31/715; A61K 8/73
See application file for complete search history.

(56) References Cited

U.S. PATENT DOCUMENTS

| | | |
|---|---|---|
| 5,460,832 A | 10/1995 | Yamaguchi et al. |
| 5,670,484 A | 9/1997 | Binder |
| 5,714,468 A | 2/1998 | Binder |
| 6,063,768 A | 5/2000 | First |
| 6,113,915 A | 9/2000 | Aoki et al. |
| 6,299,893 B1 | 10/2001 | Schwartz et al. |
| 6,358,917 B1 | 3/2002 | Carruthers et al. |
| 6,423,319 B1 | 7/2002 | Brooks et al. |
| 6,436,680 B1 | 8/2002 | Guezennec et al. |
| 6,458,365 B1 | 10/2002 | Aoki et al. |
| 6,500,436 B2 | 12/2002 | Donovan |
| 6,565,870 B1 | 5/2003 | Donovan |
| 6,623,742 B2 | 9/2003 | Voet |
| 6,641,820 B1 | 11/2003 | Donovan |
| 6,683,049 B1 | 1/2004 | Aoki et al. |
| 6,838,434 B2 | 1/2005 | Voet |
| 6,869,610 B2 | 3/2005 | Aoki et al. |
| 6,887,476 B2 | 5/2005 | Aoki et al. |
| 6,974,578 B1 | 12/2005 | Aoki et al. |
| 7,091,176 B2 | 8/2006 | Aoki et al. |
| 7,226,605 B2 | 6/2007 | Suskind et al. |
| 7,255,866 B2 | 8/2007 | Voet |
| 7,348,034 B2 | 3/2008 | Murray et al. |
| 7,465,460 B1 | 12/2008 | Gross |
| 7,468,189 B2 | 12/2008 | Aoki et al. |
| 7,473,679 B2 | 1/2009 | Blanes Mira et al. |
| 7,547,819 B2 | 6/2009 | Shibatani et al. |
| 7,553,835 B1 * | 6/2009 | Davey .................... A61K 8/046 424/1.13 |

(Continued)

FOREIGN PATENT DOCUMENTS

| | | |
|---|---|---|
| EP | 1 180 524 A1 | 2/2000 |
| EP | 1 344 528 A1 | 9/2003 |

(Continued)

OTHER PUBLICATIONS

Schaab, "Impregnating Fabrics with Microcapsules," HAPPI, pp. 84-86 (May 1986).

(Continued)

*Primary Examiner* — Gina Justice
(74) *Attorney, Agent, or Firm* — Fay Sharpe LLP

(57) ABSTRACT

Exopolysaccharide of a bacterial strain for its use in treatment and/or care of the skin, mucous membranes, hair and/or nails, as well as its cosmetic and/or dermopharmaceutical compositions. In particular, for the aging of skin and in particular for the treatment and/or prevention of wrinkles.

21 Claims, No Drawings

(56) References Cited

U.S. PATENT DOCUMENTS

| | | | |
|---|---|---|---|
| 7,695,741 B2* | 4/2010 | Lee | A61K 8/97 424/400 |
| 7,704,511 B2 | 4/2010 | Turkel et al. | |
| 7,704,524 B2 | 4/2010 | Donovan | |
| 7,811,586 B2 | 10/2010 | Brooks | |
| 8,048,423 B2 | 11/2011 | First | |
| 2009/0028924 A1 | 1/2009 | Senni et al. | |
| 2009/0117211 A1 | 5/2009 | Schneider et al. | |
| 2010/0021510 A1 | 1/2010 | Carreno Serraïma et al. | |
| 2010/0266638 A1 | 10/2010 | Turkel et al. | |
| 2011/0158922 A1* | 6/2011 | Dupont | A61K 8/73 424/59 |
| 2011/0206731 A1 | 8/2011 | First | |
| 2011/0280978 A1 | 11/2011 | Steinsapir | |
| 2011/0305647 A1 | 12/2011 | Senni et al. | |
| 2012/0148562 A1 | 6/2012 | Ho et al. | |

FOREIGN PATENT DOCUMENTS

| | | | |
|---|---|---|---|
| EP | 2 123 673 A1 | 11/2009 | |
| FR | 2 871 476 A1 | 12/2005 | |
| FR | 2 894 147 A1 | 6/2007 | |
| WO | WO 97/34620 A1 | 9/1997 | |
| WO | WO 98/38327 A1 | 9/1998 | |
| WO | WO 03/011333 A1 | 2/2003 | |
| WO | WO 2010/114828 A1 | 10/2010 | |
| WO | WO 2011/048443 A1 | 4/2011 | |

OTHER PUBLICATIONS

Raguénès, et al. "Vibrio diabolicus sp. Nov., a New Polysaccharide-Secreting Organism Isolated from a Deep-Sea Hydrothermal Vent Polychaete Annelid, Alvinella pompejana," International Journal of Systematic Bacteriology, (47) pp. 989-995 (Oct. 1997).

Stoolmiller, et al., "Chemistry and Metabolism of Macromolecules," The Journal of Biological Chemistry, pp. 236-246 (1969).

Schulz, et al., "Hyaluronan Export by the ABC Transporter MRP5 and Its Modulation by Intracellular cGMP," The Journal of Biological Chemistry, pp. 20999-21004 (2007).

Bourguignon, et al., "Hyaluronan-CD44 Interaction Stimulates Keratinocyte Differentiation, Lamellar Body Formation/Secretion, and Permeability Barrier Homeostasis," Journal of Investigative Dermatology, vol. 126, pp. 1356-1365 (2006).

Rosner, "Hyaluronic acid and a $(1 \rightarrow 4)$—$\beta$—$D$—xylan, extracellular polysaccharides of Pasteurella (Carter type A) strain 880," Carbohydrate Research, vol. 223, pp. 329-333 (1992).

Wilkinson, et al., "Harry's Cosmeticology," Seventh edition, pp. 1-36 (1982).

Burg, "Biofunctional Textiles and the Skin," Current Problems in Dermatology, vol. 33, pp. 35-41 (2006).

Volpi, et al., "Low molecular weght heparins (5 kDa) and oligoheparins (2 kDa) produced by gel permeation enrichment or radical process Comparison of structures and physicochemical and biological properties," Anal. Biochem., (200) pp. 100-107 (1992).

Nelson, G., "Application of microencapsulation in textiles," Int. J. Pharm. 2002, (242) pp. 55-62 (2002).

Hipler, et al., "Biofunctional Textiles of the Skin," Curr. Probl. Dermatol. vol. 33 pp. 1-19 (2006).

Malcom, et al., "Controlled release of a model antibacterial drug from a novel self lubricating silicone biomaterial," J. Cont. Release, (97) pp. 313-320 (2004).

Kamerling, et al., "Characterization by Gas-Liquid Chromatography-Mass Spectrometry and Proton-Magnetic-Resonance Spetroscopy of Pertrimethylsilyl Methyl Glycosides obtained in the Methanolysis of Glycoproteins and Glycopeptides," Biochem J., vol. 151, pp. 491-495 (1975).

Montreuil, et al., "Glycoproteins. In Carbohydrate analysis: a practical approach," Eds Chaplin et Kennedy, I.R.L. Press, Oxford, Washington, D.C., pp. 143-204 (1986).

Stoolmiller, et al., "The biosynthesis of hyaluronic acid by Stretococcus," J. Biol. Chem., (244) pp. 236-246 (1969).

Trabucchi, et al., "Low molecular weight hyaluronic acid prevents oxygen free radicals damage to granulation tissue during wound healing," Int. J. Tissue React., 24(2), pp. 65-71 (2002).

Matuoka, et al., "A decrease in hyaluronic acid synthesis by aging human fibroblasts leading to heparin sulfate enrichment and growth reduction," Aging, vol. 1, No. 1, pp. 47-54 (1989).

* cited by examiner

EXOPOLYSACCHARIDE FOR THE TREATMENT AND/OR CARE OF THE SKIN, MUCOUS MEMBRANES AND/OR NAILS

This application claims the benefit of PCT/EP2013/056080, filed Mar. 22, 2013, and ES 201230432, filed Mar. 22, 2012, from which the PCT application claims priority, the disclosures of which are incorporated herein by reference in their entireties.

FIELD OF THE INVENTION

The present invention relates to an exopolysaccharide (EPS), which promotes hyaluronic acid synthesis and inhibits neuronal exocytosis, and is produced by the strain of the *Vibrio* sp species with deposit number CNCM I-4277. This invention also relates to the use of this exopolysaccharide in cosmetic or dermopharmaceutical compositions for the treatment and/or care of the skin, mucous membranes, hair and/or nails.

DESCRIPTION

The skin, mucous membranes, hair and/or nails constitute a physical barrier between the organism and its environment. The skin is composed of two tissues: the epidermis and the dermis. The epidermis is the outermost layer of the skin which is impermeable and therefore provides protection from external agents. It is a keratinized pluristratified epithelium which is continually renewing itself.

The cosmetic and dermopharmaceutical industry has undertaken considerable efforts to develop compounds which are capable of maintaining the water balance of the skin, mucous membranes, hair and/or nails, and reduce wrinkles on the skin with the objective of improving its appearance, as well as its protective function and function as a barrier. One of these ingredients is hyaluronic acid; an unsulfated glycosaminoglycan of the extracellular matrix of the connective, epithelial and neuronal tissue of all vertebrates, formed by a linear polysaccharide whose units are D-glucuronic acid and D-N-acetylglucosamine. Both sugars are bound to each other by a glycosidic β-1,3 bond, but at the same time the dimers are bound by glycosidic β-1,4 bonds. Hundreds or perhaps thousands of dimers form one macromolecule with a molecular weight generally greater than 1000 KDaltons. Each one possesses an extremely high number of hydrophilic residues (hydroxyls) and a high number of negative charges (carboxyls) which results in a very hydrated, more or less rigid structure, with a consistency similar to that of a gel. In the skin, the hyaluronic acid is the viscous liquid in which the elastin and collagen and other fibers, and other intercellular structures are embedded. Hyaluronic acid is found in the extracellular matrix of human and animal tissue, and its molecular weight varies according to its location. For example, the hyaluronic acid found in the synovial liquid has a molecular weight of 1 to 8 million Daltons, that found in the human umbilical cord has a molecular weight of 3.6 to 4.5 million. However, there is an enzyme called hyaluronidase which causes depolymerization or degradation of the dimers which consist of the hyaluronic acid, what modifies the viscosity of the connective tissue.

Hyaluronic acid is the most important glycosaminoglycan in the cutaneous layer of the skin due to its contribution in the homeostasis of the skin and articulations, as well as in other vital structural biological activities for the connective tissues, such as the formation of matrixes which enable proliferation and cell migration; the regulation of immune cellular adhesion; intracellular signal activation. Hyaluronic acid is synthesized by a class of integral membrane proteins called hyaluronic acid synthases (HAS), of which vertebrates have three types: HAS1, HAS2 and HAS3. These enzymes extend the length of the hyaluronic acid polymer by the repetitive addition of glucuronic acid and N-acetylglucosamine to the nascent polysaccharide. Once synthesized, the hyaluronic acid exits into extracellular space through the cell membrane [Schulz, T. et al., "*Hyaluronan export by the ABC transporter MRP5 and its modulation by intracellular cGMP.*", *J. Biol. Chem.*, (2007), 282, 20999-21004].

Hyaluronic acid, which is naturally present in the epidermis, and in the extracellular space interacts with the receptor CD44, this interaction intervening with said receptor in the regulation of keratinocyte differentiation and the formation of extracellular lipids necessary to maintain a normal structure of the stratum corneum and the epidermal barrier function [Bourguignon L. Y. W. et al., "*Hyaluronan-CD44 Interaction Stimulates Keratonocyte Differentiation, Lamellar Body Formation/Secretion, and Permeability Barrier Homeostasis*", *Journal of Investigative Dermatology* (2006), 126, 1356-1365].

Due to its elastic and viscous properties, hyaluronic acid is capable, as well as of retaining water in the skin helping to maintain more hydrated skin, of maintaining the elasticity and reducing the formation of wrinkles, resulting in a more uniform cutaneous relief. However, the quantity of hyaluronic acid synthesized in the fibroblasts of the skin drastically reduces with age [Matuoka K. et al., "*A decrease in hyaluronic acid synthesis by aging human fibroblasts leading to heparan sulfate enrichment and growth reduction*", *Aging (Milano)*, (1989), September 1(1):47-54] and this is the cause of its loss of elasticity and formation of wrinkles and the tendency of mature skin to dry up. Hyaluronic acid exercises an important function in the prevention and reduction of wrinkles in particular of expression lines; one of the strategies more commonly used by the cosmetic and dermopharmaceutical industry for the treatment of wrinkles is the administration, both topical and subcutaneous, of hyaluronic acid due to its ability to absorb water and therefore to fill out the wrinkle from the inside of the skin.

On the other hand, another strategy for the prevention and reduction of wrinkles, in particular expression lines, is the administration of compounds which block the muscle contraction by inhibition of the neuronal exocytosis on that area. The principle muscles involved in the appearance of expression lines are those surrounding the eyes and eyelashes, those on the forehead, the lip, mouth, cheek and neck muscles. These muscles are found in the subcutaneous connective frontal part of the face, from where they rise towards the skin and insert themselves in the deepest part of the dermal stratum. Their contraction can lead to raising, depressing, constricting or dilatory movements of the skin.

Since the 1990s, the use of the toxins *Clostridium botulinum* (marketed as Botox® by Allergan) injected into the muscle to reduce muscle contraction and to treat associated diseases such as dystonia and/or pain. Neurotoxin injections have also been used to treat and/or care for the skin with the aim of reducing, delaying or preventing the signs of aging and/or photoaging and in particular to relax the facial expression and reduce the formation of wrinkles or minimize their appearance. Its action mechanism is based on blocking ACh release in the presynaptic terminal of the axon in the neuromuscular junction, thus avoiding nerve transmission and muscle contraction. The toxin binds to receptors in the presynaptic membrane, is internalized and becomes cytoplasm. Its activity is responsible for breaking the trimolecular synaptobrevin SNARE complex, SNAP-25 and syntaxin, which avoids the binding of synaptic vesicles to plasmalemma and releasing ACh to the synaptic cleft. The controlled administration of the botulinum toxin has been used for the treatment of a wide range of conditions, disorders and diseases, such as perspiration and hyperhidrosis (U.S. Pat. No. 6,974,578 B2 and U.S. Pat. No. 6,683,049 B2), disorders and diseases of the skin such as calluses, warts, ulcers and lesions on the skin (U.S. Pat. No. 8,048,423 B2, US 2011/206731), psoriasis and dermatitis (U.S. Pat. No. 5,670,484 A), vascular hyperreactivity and rosacea (WO 2010/114828), acne (WO 03/011333), hair growth and maintenance (U.S. Pat. No. 6,299,893 B1), ptosis of the eyebrows and forehead (US 2011/280978), drooping mouth corners (U.S. Pat. No. 6,358,917 B1) or different types of pain and inflammation (US 2010/266638, U.S. Pat. No. 7,811,586 B2, U.S. Pat. No. 7,704,524 B2, U.S. Pat. No. 7,704,511 B2, U.S. Pat. No. 7,468,189 B2, U.S. Pat. No. 7,255,866 B2, U.S. Pat. No. 7,091,176 B2, U.S. Pat. No. 6,887,476 B2, U.S. Pat. No. 6,869,610 B2, U.S. Pat. No. 6,838,434 B2, U.S. Pat. No. 6,641,820 B2, U.S. Pat. No. 6,623,742 B2, U.S. Pat. No. 6,565,870 B1, U.S. Pat. No. 6,500,436 B1, U.S. Pat. No. 6,458,365 B1, U.S. Pat. No. 6,423,319 B1, U.S. Pat. No. 6,113,915 A, U.S. Pat. No. 5,714,468 A and U.S. Pat. No. 6,063,768 B2) among others.

Furthermore, various applications of hyaluronic acid on its own or reticulated with a variety of different molecules have been found. Particularly, it can be used to prevent the action of the free radicals during wound healing [Trabucchi E. et al., "*Low molecular weight hyaluronic acid prevents oxygen free radicals damage to granulation tissue during wound healing*", *Int. J. Tissue React*., (2002), 24(2), 65-71], and also as filler material in aesthetic surgery in implants and fillers.

Hyaluronic acid has also been found in other species as well as in humans. Hyaluronic acid is abundant in chicken combs, shark fins, in the ocular vitreous body and in secretions such as liquid between mammal's joints. It is also present in bovine vitreous humor, in the connective tissue of numerous organisms and in certain bacterial strains such as those of the genus *Streptococcus* [Stoolmiller et al., "*The biosynthesis of hyaluronic acid by Streptococcus*", *J. Biol. Chem*., (1969), 244, 236-246] and *Pasteurella* [Rosner et al., "*Hyaluronic acid and a* (1-4)-*beta-D-xylan, extracellular polysaccharides of Pasteurella multocida* (*Carter type A*) *strain* 880", *Carbohdr. Res*., (1992), 223, 329-333], and in extracts of bacteria such as *Samphire Crithmum maritimum*, which produce it by emulating animal tissues as a way of protecting themselves from the attack of the immune system of animals that they infect. Thus, the production of hyaluronic acid is possible from the fermentation of bacteria which produce it naturally.

The chemical composition and structure of hyaluronic acid is the same, regardless of its animal or bacterial origin, and can only be differentiated by its molecular weight due to the action of the hyaluronidases present in bacteria cultures. Therefore, the bacterial strains which lack hyaluronidase are desirable in order to ensure a minimal degradation of hyaluronic acid. Consequently, hyaluronic acid of animal origin can replace materials of animal origin provided that their purity and weight are satisfactory.

The properties of hyaluronic acid depend on the molecular weight; hyaluronic acid with a high molecular weight has structural properties, whilst the degradation products of hyaluronic acid or low molecular weight hyaluronic acid stimulate the proliferation of endothelial cells and migration, they modulate inflammatory processes and promote neo-angiogenesis during the different stages of wound healing. Instead, hyaluronic acid with a low molecular weight can cross the cutaneous barrier and improve the elasticity of the perivascular tissue, which increases the blood flow, reduces couperose and reinforces the capillaries to stop the edema which accompanies cellulitis.

Within the cosmetic industry there is an interest in promoting the metabolic function of the skin which carries out the production of hyaluronic acid. Thus, for example, patent EP 1344528 B1 describes the effect of epidermal cell activation and the increase in the production of hyaluronic acid which possess vitamin A and its derivatives, when they are combined with a fermented product obtained by the microorganisms of the genus *Bifidobacterium* which react with a bean extract. Other extracts such as chia seed oil, *Opuntia ficus, Wolfberry, Angelica China*, or extract of wild rose Cherokee, *Eribotrya Japonica* and grape seed have been described in patents US 2009/117211 A1 and U.S. Pat. No. 7,348,034 B1 to improve the humidity, texture and appearance of the skin, by increasing the macromolecules found in the extracellular matrix of the skin, such as hyaluronic acid or glycosaminoglycans in general. Another example is U.S. Pat. No. 5,460,832 A, which describes a cosmetic composition with anti-aging and moisturizing properties caused by an egg white enzyme hydrolyzate capable of promoting hyaluronic acid synthesis in dermal fibroblasts. U.S. Pat. No. 7,465,460 B1 includes daidzein in its dermatological composition with the same purpose of promoting hyaluronic acid synthesis. Furthermore, U.S. Pat. No. 7,547,819 B2, describes a method through which genetically modified plants with a DNA encoding a hyaluronic acid synthase are capable of synthesizing hyaluronic acid.

The cosmetic industry has also carried out different efforts to develop new compounds for the treatment of expression lines by inhibition of the neuronal exocytosis. In particular, peptides derived from the amino terminal fragment of the protein SNAP-25 which have anti-wrinkle effects are described in the documents EP 1180524 A1 and EP 2123673 A1; the international application WO 97/34620 also describes peptides derived from the sequence of amino acids of the protein SNAP-25, in particular from its carboxy-terminal region, or from the synaptobrevin or the syntaxin capable of inhibiting neuronal exocytosis; and the international application WO 2011/048443 describes peptides derived from the subunit c of the membrane component of V-ATPase capable of inhibiting neuronal exocytosis through its bonding to synaptobrevin and its potential application as anti-wrinkle treatment.

Surprisingly the applicant of this invention has found a new alternative to the compounds described in the prior art based on a new exopolysaccharide produced by the bacterial strain *Vibrio* sp. with deposit number CNCM I-4277 according to the Budapest Treaty which promotes hyaluronic acid synthesis and inhibits neuronal exocytosis and therefore improves the hydration of the skin, mucous membranes, hair and/or nails and prevents and/or reduces wrinkles on the skin. Furthermore the exopolysaccharide has been found to be useful for the treatment and/or care of conditions, disorders and/or diseases which improve or are prevented by the inhibition of neuronal exocytosis.

DETAILED DESCRIPTION OF THE INVENTION

This invention relates to the exopolysaccharide produced by the bacterial strain *Vibrio* sp. with deposit number CNCM I-4277 for its cosmetic and/or dermopharmaceutical use. Surprisingly the inventors of this invention have found that the aforementioned exopolysaccharide promotes hyaluronic acid synthesis and inhibits neuronal exocytosis. In particular, the stimulation of hyaluronic acid improves the hydration of the skin, mucous membranes, hair and/or nails, improves the flexibility of the skin and evens out the surface of the skin. On the other hand, the inhibition of neuronal exocytosis has been found to be useful for the prevention and/or reduction of wrinkles, particularly, expression lines.

DEFINITIONS

In order to facilitate the comprehension of this invention, the meanings of some terms and expressions as used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as marks, reddening, bags under the eyes or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and present the same physical characteristics as aging, such as and not restricted to, flaccidity, sagging, changes of color or irregularities in the pigmentation, abnormal and/or excessive keratinization.

The strain which produces the exopolysaccharide of this invention was deposited in accordance with the Budapest Treaty, on 17 Feb. 2010, in the "Collection Nationale de Culture de Microorganismes" [National Microorganism Culture Collection] (CNCM), Institut Pasteur, 28 rue du Docteur Roux, 75724 Paris, France, under code CNCM I-4277.

Thus, a first aspect of this invention relates to the exopolysaccharide of the strain of the *Vibrio* sp. species with deposit number CNCM I-4277 for its use in the treatment and/or care of the skin, mucous membranes, hair and/or nails.

In a particular embodiment the treatment and/or care of the skin, mucous membranes, hair and/or nails is a treatment and/or prevention of aging, preferably it is a treatment and/or prevention of wrinkles on the skin, and more preferably it is a filling treatment of wrinkles on the skin or is a treatment and/or prevention of expression wrinkles.

In a particular embodiment the treatment and/or care of the skin, mucous membranes, hair and/or nails stimulates hyaluronic acid synthesis.

In a particular embodiment the treatment and/or care of the skin, mucous membranes, hair and/or nails inhibits neuronal exocytosis.

In another particular embodiment the treatment and/or care of the skin, mucous membranes, hair and/or nails is a treatment and/or care of conditions, disorders and/or diseases which are a result of the lack or decrease in hydration of the skin, mucous membranes, hair and/or nails. Preferably the conditions, disorders and/or diseases are selected from the group formed by dry skin, xerosis, hyperkeratosis, reactive hyperkeratosis, palmar and plantar hyperkeratosis, corns or calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, couperose, vaginal dryness, ocular dryness, dry hair, brittle hair and nails.

In another particular embodiment, the treatment and/or care of the skin, mucous membranes, hair and/or nails is a treatment and/or care of conditions, disorders and/or diseases that are a result of inflammation of the skin, mucous membranes and/or nails. Preferably the conditions, disorders and/or diseases are selected from the group formed by sensitive skin, dermatitis, atopic dermatitis, contact dermatitis, diaper dermatitis, seborrheic dermatitis, eczema, hyperproliferative skin disease, burns, sunburn, paronychia, inflammation of the mucous membrane of the vagina, inflammation of the oral mucous membranes, gingivitis, periodontitis.

In another particular embodiment the treatment and/or care of the skin, mucous membranes, hair and/or nails is a reepithelizing and/or healing treatment of the skin and/or mucous membranes.

In another particular embodiment, the treatment and/or care of the skin, mucous membranes, hair and/or nails is a treatment and/or prevention of pain of the skin, mucous membranes and/or nails. Preferably, the pain is selected from pain associated with conditions, diseases and/or disorders, for example and not restricted to, touch sensitivity, sensitivity to cold, sensitivity to heat, cutaneous irritation, post-hair removal cutaneous irritation, post-shaving cutaneous irritation, psoriasis, sensitive skin, dermatitis, atopic dermatitis, contact dermatitis, diaper dermatitis, seborrheic dermatitis, eczema, lichen planus, burns, sunburn, arthritis, rheumatoid arthritis, osteoarthritis, psoriatic arthritis, hypersensitivity, cutaneous pain or irritation after surgery, after intense pulsed light treatment (IPL), after treatment with monochromatic pulsed light (laser), after a treatment with chemical desquamating agents or after overexposure to external aggressive agents, among others.

In another particular embodiment, the treatment and/or care of the skin, mucous membranes, hair and/or nails is a treatment and/or prevention of itching of the skin, mucous membranes and/or nails. Preferably, the itching is selected from itching associated with conditions, diseases and/or disorders, for example and not restricted to, dermatitis, atopic dermatitis, contact dermatitis, diaper dermatitis, dermatitis herpetiformis, photodermatosis, photosensitivity, pregnancy related dermatitis, menopause related dermatitis, eczema, sensitive skin, psoriasis, chickenpox, herpes, herpes zoster, Netherton's syndrome, peeling skin syndrome, lichen planus, acne, dandruff, seborrhea, seborrheic dermatitis, alopecia, athlete's foot, candidiasis, hemorrhoids, vaginal itching, perianal itching, anogenital itching, sunburn, hives, pruritic otitis, itchy eyes, senile pruritus, aquagenic pruritus, prurigo nodularis, prurigo planus, pityriasis rosea, xerosis and dry skin, allergic reactions, allergies to medicines, food allergies, allergies to chemical products, exposure to poisonous plants and exposure to insect bites, among others.

In a particular embodiment the treatment and/or care of the skin, mucous membranes, hair and/or nails is a treatment and/or prevention of hyperhidrosis.

In another particular embodiment the treatment and/or care of the skin, mucous membranes, hair and/or nails is a treatment of elimination and/or prevention of the formation of free radicals.

In a particular embodiment the treatment and/or care of the skin, mucous membranes, hair and/or nails is a treatment and/or prevention of perspiration, treatment and/or care of disorders of the skin selected from the group formed by calluses or warts, treatment stimulating hair growth and/or prevention of hair loss.

Preferably, the treatment and/or prevention of hyperhidrosis or perspiration, is a treatment and/or prevention of axillary, facial, genital, palmar or plantar hyperhidrosis or perspiration.

In another particular embodiment the treatment and/or care of the skin, mucous membranes, hair and/or nails is carried out by topical or transdermal application.

In another particular embodiment, the exopolysaccharide can be obtained through fermentation of the bacterial strain *Vibrio* sp. with deposit number CNCM I-4277 in a suitable culture medium, conventionally stirred and aerated. Fermentation to produce the exopolysaccharide of this invention can be carried out in a medium stirred and aerated at a temperature between 20° C. and 37° C., preferably at 29° C., the medium having a pH between 6.5 and 9, preferably around 7.5, adjusting it if necessary during fermentation. The duration of the fermentation is between 30 to 120 hours, preferably between 48 and 96 hours.

In a particular embodiment, in the fermentation of the bacterial strain *Vibrio* sp. of the invention exogenous sugars, such as and not restricted to, galactose, glucose, mannose, amygdalin, cellobiose, maltose, starch, glycogen, lactose, mixtures thereof and/or extracts containing mixtures of these sugars can be used as a source of carbon. In particular, an exogenous supply of glucose of 2 to 40 g/L, and preferably from 15 to 25 g/L, is provided. Methods of incorporation of sugars to produce different polysaccharides are described in the prior art, such as and not restricted to documents: WO 98/38327, and "*Vibrio diabolicus sp. nov., a new polysaccharide-secreting organism isolated from a deep-sea hydrothermal vent polychaete annelid, Alvinella pompejana*" Raguénès et al., Int. J. Syst. Bact., (1997), 47, 989-995.

In another particular embodiment, mineral salts are also provided for the fermentation culture of the strain of the *Vibrio* sp. species with deposit number CNCM I-4277. For example and not restricted to, they are selected from among salts which provide the ions $Na^+$, $K^+$, $NH_4^+$, $Ca^{2+}$, $Mg^{2+}$, $PO_4^{3-}$, $SO_4^{2-}$, $Cl^-$, $CO_3^{2-}$, or essential trace elements such as Cu, Mn, Fe and Zn.

In another particular embodiment, the method of isolation and purification of the exopolysaccharide is carried out by the methods known by the person skilled in the art such as, centrifugation, filtration, ultrafiltration and dialysis. Preferably, ultrafiltration and dialysis are carried out with a polyethersulfone membrane which retains molecules of a molecular weight greater than 100,000 Da.

In another particular embodiment, the exopolysaccharide produced by the strain of the *Vibrio* sp. species with deposit number CNCM I-4277, presents a natural sulfatation without mediating any chemical modification of up to 7% of sulfates, more preferably up to 5% of sulfates.

In another particular embodiment this invention relates to the native exopolysaccharide as well as any chemical modification known by the person skilled in the art such as phosphorylation, sulfonation, acylation with for example acetyl, pyruvoyl, propionyl, succinyl, lactoyl or 3-hydroxybutyl groups, esterification with for example glyceryl, formation of metallic complexes of the exopolysaccharide and/or chemical sulfatation greater than 7%.

The molecular weight of the polysaccharide is comprised between 100,000 and 10 million Da, and more preferably between 100,000 and 5 million Da. In a particular embodiment, a radical depolymerization is carried out wherein the molecular weight is between 100,000 and 1 million Da. Depolymerization methods are known in the prior art, for example and not restricted to those described in [Volpi et al., "*Low molecular weight heparins (5 kDa) and oligoheparins (2 kDa) produced by gel permeation enrichment or radical process: Comparison of structures and physicochemical and biological properties.*", Anal. Biochem., (1992), 200, 100-107].

In a preferred embodiment, the exopolysaccharide produced by the strain of the *Vibrio* sp. species with deposit number CNCM I-4277 is characterized by presenting at least three different neutral monosaccharides and one acid monosaccharide. The neutral monosaccharides are preferably fucose, glucose, and N-acetylglucosamine. The monosaccharide acid is preferably glucuronic acid. More preferably, the exopolysaccharide of this invention presents a composition in weight of 1% to 12% of fucose, 10% to 35% of glucose, 18% to 40% of glucuronic acid, and 34% to 56% of N-acetylglucosamine, with the condition that the sum of the percentages does not exceed 100%. Even more preferably, the exopolysaccharide presents a composition in weight of 2% to 10% of fucose, 14% to 30% of glucose, 22% to 35% of glucuronic acid, and 38% to 52% of N-acetylglucosamine. Even more preferably, the exopolysaccharide presents a composition in weight of 3% to 8% of fucose, 18% to 22% of glucose, 27% to 30% of glucuronic acid, and 45% to 49% of N-acetylglucosamine.

A second aspect of this invention relates to a cosmetic or dermopharmaceutical composition characterized in that it comprises a cosmetically or dermopharmaceutically effective quantity of the exopolysaccharide of this invention and at least one excipient, adjuvant and/or cosmetically and/or dermopharmaceutically acceptable ingredient. Said compositions can be prepared by the conventional methods known by the persons skilled in the art ["*Harry's Cosmeticology*", Seventh edition, (1982), Wilkinson J. B., Moore R. J., ed. Longman House, Essex, GB].

The cosmetically or dermopharmaceutically effective quantity of the exopolysaccharide in the invention to be administered, as well as its dosage, will depend on numerous factors, including age, condition of the patient, the nature or severity of the condition, disorder or disease to be treated and/or cared for, the route and frequency of administration and the nature, in particular, of the exopolysaccharides to be used.

"Cosmetically or dermopharmaceutically effective amount" is understood to be a non-toxic but sufficient quantity of the exopolysaccharide to provide the desired effect. The exopolysaccharide of the invention is preferably used, with regard to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight).

In a particular embodiment, the exopolysaccharide of the invention can also be incorporated into cosmetic and/or dermopharmaceutical delivery systems and/or sustained release systems.

The term "delivery systems" relates to a cosmetically and/or dermopharmaceutically acceptable carrier such as a diluent, adjuvant, excipient, vehicle or additives with which the exopolysaccharide of the invention is administered. These delivery systems are well known in the prior art and can be used, for example, to improve the definitive formulation with regard to organoleptic properties, penetration of the skin and the bioavailability of the active ingredient. These cosmetic and/or dermopharmaceutical vehicles can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants, excipients or additives which can be used in the different delivery systems in which the exopolysaccharide is administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems are liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as microemulsions and nanoemulsions, which can be added to achieve a greater penetration of the exopolysaccharide of the invention. Preferred delivery or sustained release systems are liposomes, surfactant-phospholipid mixed micelles and microemulsions, more preferably water-in-oil microemulsions with an internal reverse micelle structure and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, and preferably should release a relatively constant quantity of the exopolysaccharide of the invention. The amount of exopolysaccharide contained in the sustained release system will depend, for example, on where the composition is to be administered, the kinetics and duration of the release of the exopolysaccharide of the invention, as well as the nature of the condition, disorder and/or disease to be treated and/or cared for.

The composition containing the exopolysaccharide of this invention can also be adsorbed on solid organic polymers or solid mineral supports, such as and not restricted to, talc, bentonite, silica, starch or maltodextrin among others.

The compositions containing the exopolysaccharide of the invention can also be incorporated into fabrics, non-woven fabrics or medical devices which are in direct contact with the skin, thus releasing the exopolysaccharide of the invention whether by biodegradation of the binding system to the fabric, non-woven fabric or medical device, or due to the friction between them and the body, due to body moisture, the skin's pH or body temperature. Furthermore, the exopolysaccharide of the invention can be incorporated into the fabrics and non-woven fabrics used in the manufacture of garments that are in direct contact with the body.

Examples of fabrics, non-woven fabrics, garments, medical devices and means for immobilizing the exopolysaccharide to them, among which are the delivery systems and/or the sustained release systems described above, can be found in literature and are known in the prior art (Schaab C. K. 1986 "Impregnating Fabrics With Microcapsules", HAPPI May 1986; Nelson [Schaab C. K. 1986 "Impregnating Fabrics With Microcapsules", HAPPI May 1986; Nelson G. Int. J. Pharm. 2002, 242:55-62; Hipler U. C. and Elsner P. 2006, "Biofunctional Textiles and the Skin", Curr. Probl. Dermatol. v. 33, eds. S. Karger A G, Basel, Switzerland; Malcom R. K. et al. J. Cont. Release, 2004, 97:313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or dermopharmaceutical compositions containing the exopolysaccharide of this invention can be used in different types of compositions of topical or transdermal application, optionally including cosmetically and/or dermopharmaceutically acceptable excipients necessary for formulating the desired administration form.

Compositions of topical or transdermal application can be produced in any solid, liquid or semisolid formulation. Thus, these compositions of topical or transdermal application are, for example and not restricted to, multiple emulsions, such as and not restricted to, oil and/or silicone in water emulsions, water-in-oil and/or silicone emulsions, water/oil/water or water/silicone/water type emulsions, and oil/water/oil or silicone/water/silicone type emulsions, microemulsions, liquid crystals, anhydrous compositions, aqueous dispersions, oils, milks, balsams, foams, aqueous or oily lotions, aqueous or oily gels, creams, solutions, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils and sprays or aerosols (sprays), including leave-on and rinse-off formulations. These formulations are topically or transdermally applied on local areas of the skin, mucous membranes, hair and/or nails and can be incorporated using techniques known by the person skilled in the art into different types of solid accessories, such as and not restricted to, bandages, gauzes, t-shirts, socks, tights, underwear, girdles, gloves, diapers, sanitary napkins, dressings, bedspreads, flannels, adhesive patches, non-adhesive patches, occlusive patches, microelectric patches and/or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or dermopharmaceutical compositions of the invention may include agents which increase the percutaneous absorption of the exopolysaccharide of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or dermopharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the exopolysaccharide of the invention. The application area will be determined by the nature of the condition, disorder and/or disease to be treated and/or cared for.

Among the cosmetically or dermopharmaceutically acceptable excipients, adjuvants and/or ingredients contained in the cosmetically or dermopharmaceutically acceptable compositions described in this invention are additional ingredients commonly used in compositions for the treatment and/or care of the skin, mucous membranes, hair and/or nails such as and not restricted to, other hyaluronic acid synthesis-stimulating agents, glycosaminoglycan synthesis-stimulating agents, collagen synthesis-stimulating agents, agents stimulating the synthesis of dermal or epidermal macromolecules and/or capable of inhibiting or preventing their degradation, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, heat shock proteins, HSP70 synthesis-stimulating agents, heat shock protein synthesis-stimulating agents, fibronectin synthesis-stimulating agents, sirtuin synthesis-stimulating agents, sirtuin activating agents, agents stimulating the synthesis of lipids and components of the stratum corneum, ceramides, fatty acids, agents that inhibit collagen degradation, agents that inhibit elastin degradation, agents that inhibit serine proteases such as kallikreins, leukocyte elastase, cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents inhibiting acetylcholinesterase, skin relaxant agents, agents modulating AQP-3, agents modulating aquaporin synthesis, proteins from the aquaporin family, agents that modulate PGC-la synthesis, agents modulating PPARγ activity, agents that increase or reduce the triglyceride content of adipocytes, agents stimulating or delaying adipocyte differentiation lipolytic agents or agents stimulating lipolysis, anti-cellulite agents, adipogenic agents, agents inhibiting acetylcholine receptor clustering, muscle contraction inhibiting agents, inhibitors of neuronal exocytosis, anti-wrinkle and/or antiaging agents, anticholinergic agents, elastase inhibiting agents, matrix metalloprotease inhibiting agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl or oxygen species scavengers, anti-glycation agents, antihistamine agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat bags under the eyes, exfoliating agents, desquamating agents, keratolytic agents, antimicrobial agents, antifungal agents, fungistatic agents, bactericidal agents, bacteriostatic agents, antihyperkeratosis agents, comedolytic agents, anti-psoriasis agents, anti-dermatitis agents, anti-eczema agents, DNA repairing agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, cosmetic deodorant agent and/or body odor absorbent agent and/or body odor masking agent and/or antiperspirant agent, scented substance and/or scented oil, agents stimulating healing, coadjuvant healing agents, agents stimulating reepithelialization, coadjuvant reepithelialization agents, cytokine growth factors, calming agents, anti-inflammatory agents and/or analgesics, anesthetic agents, PAR-2 activity inhibiting agents, agents acting on capillary circulation and/or microcirculation, agents stimulating angiogenesis, agents inhibiting vascular permeability, venotonic agents, agents acting on cell metabolism, agents to improve dermal-epidermal junction, agents inducing hair growth, hair growth inhibiting or retardant agents, perfumes, chelating agents, plant extracts, essential oils, marine extracts, agents obtained from a biofermentation process, mineral salts, cell extracts, sunscreens and organic or mineral photoprotective agents active against ultraviolet A and/or B rays, or mixtures thereof among others, provided that they are physical and chemically compatible with the rest of components of the composition and in particular with the exopolysaccharide contained in the composition of this invention. Furthermore, the nature of these additional ingredients should not unacceptably alter the benefits of the exopolysaccharide of this invention. The nature of said additional ingredients can be synthetic or natural in origin, such as plant extracts, or come from a biotechnological process or from a combination of a synthetic procedure and biotechnological process. Additional examples can be found described in *CTFA International Cosmetic Ingredient Dictionary & Handbook*, 12th Edition (2008). In the context of this invention, biotechnological process is understood to be any process that produces the active ingredient, or part thereof, in an organism, or in a part thereof.

In a particular embodiment, the humectant or substance that retains moisture, moisturizer or emollient is selected, for example and not restricted to, from the group formed by polyols and polyethers such as glycerin, ethylhexylglycerin, caprylyl glycol, pentylene glycol, butylene glycol, propylene glycol and its derivatives, triethylene glycol, polyethylene glycol, Glycereth-26, Sorbeth-30; panthenol; pyroglutamic acid and its salts and derivatives; amino acids, such as serine, proline, alanine, glutamate or arginine; ectoin and its derivatives; N-(2-hydroxyethyl)acetamide; pyrrolidone carboxylic acid (PCA); N-lauroyl-pyrrolidone carboxylic acid; N-lauroyl-L-lysine; N-alpha-benzoyl-L-arginine; urea; creatine; alpha- and beta-hydroxyacids such as lactic acid, glycolic acid, malic acid, citric acid, tartaric acid or salicylic acid, and their salts; polyglyceryl acrylate; sugars and polysaccharides, such as glucose, isomerate saccharide, sorbitol, pentaerythritol, inositol, xylitol, sorbitol, trehalose and its derivatives, sodium glucuronate, carraghenates (*Chondrus crispus*) or chitosan; glycosaminoglycans such as hyaluronic acid and its derivatives; *aloe vera* in any of its forms; honey; soluble collagen; lecithin and phosphatidylcholine; ceramides; cholesterol and its esters; tocopherol and its esters, such as tocopheryl acetate or tocopheryl linoleate; long chain alcohols such as cetearyl alcohol, stearyl alcohol, cetyl alcohol, oleyl alcohol, isocetyl alcohol or octadecan-2-ol; long chain alcohol esters such as lauryl lactate, myristyl lactate or $C_{12}$-$C_{15}$ alkyl benzoate; fatty acids such as stearic acid, isostearic acid or palmitic acid; polyunsaturated fatty acids (PUFAs); sorbitans such as sorbitan distearate; glycerides such as glyceryl monoricinoleate, glyceryl monostearate, glyceryl stearate citrate or caprylic acid and capric acid triglyceride; saccharose esters such as saccharose palmitate or saccharose oleate;

butylene glycol esters, such as dicaprylate and dicaprate; fatty acids such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ehtylhexyl palmitate, 2-ethylhexyl cocoate, decyl oleate, myristyl myristate; squalane, squalene; mink oil; lanolin and its derivatives; acetylated lanolin alcohols; silicon derivatives such as cyclomethicone, dimethicone or dimethylpolysiloxane; Antarcticine®[INCI: *Pseudoalteromonas* Ferment Extract], Xpertmoist™ [INCI: Glycerin, *Pseudoalteromonas* Ferment Extract, Xanthan Gum, Proline, Alanine, Serine, Ethylhexylglycerin, Caprylyl Glycol], Bodyfensine™ [INCI: Acetyl Dipeptide-3 Aminohexanoate], Diffuporine™ [INCI: Acetyl Hexapeptide-37] or Hyadisine™ [INCI: *Pseudoalteromonas* Ferment Extract] marketed by Lipotec; petrolatum; mineral oil; mineral and synthetic waxes; beeswax (*cera alba*); paraffin; or waxes and oils of vegetable origin such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose seed oil (*Rosa moschata*), wild soybean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), and/or mixtures thereof, among others.

In a particular embodiment, the agent stimulating hyaluronic acid synthesis, agents stimulating glycosaminoglycan synthesis is selected, for example and not restricted to, from the group formed by extracts of bacteria from the genus *Streptococcus, Pasteurella*, and *Sampire Crithmum* and vitamin A and its derivatives, microorganisms from the genus *Bifidobacterium*, extract of chia oil, extract of *Opuntia ficus*, extract of *Lycium barbarum*, extract of *Angelica China*, extract of wild Cherokee rose or extract of grape seed, among others.

In a particular embodiment, the agent stimulating the synthesis of dermal or epidermal macromolecules is selected, for example and not restricted to, from the group formed by collagen synthesis-stimulating agents, elastin synthesis-stimulation agents, decorin synthesis-stimulation agents, laminin synthesis-stimulation agents, chaperone synthesis-stimulating agents, sirtuin synthesis-stimulating agents, sirtuin activating agents, aquaporin synthesis-modulating agents, fibronectin synthesis-stimulating agent, agents that inhibit collagen degradation, agents that inhibit elastin degradation, agents that inhibit serine proteases such as kallikreins, leukocyte elastase or cathepsin G, agents stimulating fibroblast proliferation, agents stimulating adipocyte proliferation, agents that accelerate or delay adipocyte differentiation, and DNA repairing agents and/or DNA protecting agents, such as and not restricted to extracts of *Centella asiatica, Saccharomyces cerivisiae, Solanum tuberosum, Rosmarinus officinalis, Vaccinium angustifolium*, extract of the algae *Macrocystis pyrifera, Padina pavonica*, extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of saline zooplankton, the fermentation product of milk with *Lactobacillus Bulgaricus*, asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: *Pseudoalteromonas* Ferment Extract], Decorinyl® [INCI: Tripeptide-10 Citrulline], Serilesine® [INCI: Hexapeptide-10], Lipeptide [INCI: Hydrolized Vegetable Protein], Aldenine® [INCI: Hydrolized Wheat Protein, Hydrolized Soy Protein, Tripeptide-1], Relistase™ [INCI: Acetylarginyltryptophyl Diphenylglycine], Thermostressine™ [INCI: Acetyl Tetrapeptide-22], Peptide AC29 [INCI: Acetyl Tripeptide-30 Citrulline], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Adifyline™[INCI: Acetyl Hexapeptide-38] marketed by Lipotec, Drieline® PF [INCI:Yeast Betaglucan] marketed by Alban Muller, Phytovityl C® [INCI: Aqua, *Zea Mays* Extract] comercializado por Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, minerals such as calcium, among others, retinoids and their derivatives, isoflavonoids, carotenoids, in particular lycopene, pseudodipeptides, retinoids and their derivatives such as retinol or retinyl palmitate, among others, or heparinoids, among others.

In a particular embodiment, the anti-wrinkle and/or anti-aging agent is selected, for example and not restricted to, from the group formed by extracts or hydrolyzed extracts of *Vitis vinifera, Rosa canina, Curcuma longa, Theobroma cacao, Ginkgo biloba, Leontopodium alpinum* or *Dunaliella salina* among others; Matrixyl® [INCI: Palmitoyl Pentapeptide-4], Matrixyl 3000® [INCI: Palmitoyl Tetrapeptide-7, Palmitoyl Oligopeptide], Essenskin™ [INCI: Calcium Hydroxymethionine], Renovage [INCI: Teprenone] or Dermaxyl® [INCI: Palmitoyl Oligopeptide] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia Siliqua*) Gum] or Preregen® [INCI: *Glycine Soja* (Soybean) Protein, Oxido Reductases] marketed by Pentapharm/DSM, Myoxinol™ [INCI: Hydrolyzed Hibiscus *Esculentus* Extract], Syniorage™[INCI: Acetyl Tetrapeptide-11], Dermican™ [INCI: Acetyl Tetrapeptide-9] or DN AGE™ LS [INCI: *Cassia Alata* leaf Extract] marketed by Laboratoires Sérobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolized Wheat Protein, Hydrolized Soy Protein, Tripeptide-1], Preventhelia™ [INCI: Diaminopropionoyl Tripeptide-33], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI: Acetylarginyltryptophyl Diphenylglycine], Thermostressine® [INCI: Acetyl Tetrapeptide-22], Lipochroman™ 6 [INCI: Dimethylmethoxy Chromanol], Chromabright™ [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide 10 Citrulline], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Adifyline™[INCI: Acetyl Hexapeptide-38], Hyadisine™ [INCI: *Pseudoalteromonas* Ferment Extract] or Delisens™ [proposed INCI: Acetyl Hexapeptide-46] marketed by Lipotec, Kollaren® [INCI: Tripeptide 1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP/Ashland, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella Oleracea* Extract], Gatuline® In-Tense [INCI: Spilanthes *Acmella* Flower Extract] or Gatuline® Age Defense 2 [INCI: *Juglans Regia* (Walnut) Seed Extract] marketed by Gattefossé, Thalassine™[INCI: *Algae* Extract] marketed by Biotechmarine, ChroNOline™ [INCI: Caprooyl Tetrapeptide-3] or Thymulen-4 [INCI: Acetyl Tetrapeptide-2] marketed by Atrium Biotechnologies/Unipex Innovations, EquiStat [INCI: *Pyrus Malus* Fruit Extract, *Glycine Soja* Seed Extract] or Juvenesce [INCI: Ethoxydiglicol and Caprylic Triglycerid, Retinol, Ursolic Acid, Phytonadione, Ilomastat] marketed by Coletica/Engelhard/BASF, Ameliox [INCI: Carnosine, Tocopherol, *Silybum Marianum* Fruit Extract] or PhytoCellTec *Malus Domestica* [INCI: *Malus Domestica* Fruit Cell Culture] marketed by Mibelle Biochemistry, Bioxilift [INCI: *Pimpinella Anisum* Extract] or SMS Anti-Wrinkle® [INCI: *Annona Squamosa* Seed Extract] marketed by Silab, antagonists of the Ca$^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repairing enzymes such as and not restricted to, photolyase or T4 endonuclease V, or chloride channel agonists, among others.

Furthermore, in another particular embodiment, the agent stimulating healing, coadjuvant healing agent, agent stimulating reepithelialization and/or coadjuvant reepithelialization agent is selected, for example and not restricted to, the group formed by extracts of *Aristoloquia clematis, Centella asiatica, Rosa moschata, Echinacea angustifolia, Symphytum officinal, Equisetum arvense, Hypericum perforatum, Mimosa tenuiflora, Persea gratisima, Prunus africanum, Tormentilla erecta, Aloe vera*, Polyplant® Epithelizing [INCI: *Calendula Officinalis, Hypericum Perforatum, Chamomilla Recutita, Rosmarinus Officinalis*] marketed by Provital, Cytokinol® LS 9028 [INCI: Hydrolyzed Casein, Hydrolyzed Yeast Protein, Lysine HCl] marketed by Laboratories Sérobiologiques/Cognis/BASF or Deliner® [INCI: *Zea Mays* (Corn) Kernel Extract] marketed by Coletica/Engelhard, allantoin, cadherins, integrins, selectins, hyaluronic acid receptors, immunoglobulins, fibroblast growth factors, connective tissue growth factors, platelet-derived growth factors, vascular endothelial growth factors, epidermal growth factors, insulin-like growth factor, keratinocyte growth factors, colony-stimulating factors, transforming growth factor-beta, tumor necrosis factor-alpha, interferons, interleukins, matrix metalloproteases, receptor protein tyrosine phosphatases, Antarcticine® [INCI: *Pseudoalteromonas* Ferment extract], Bodyfensine® [INCI: Acetyl Dipeptide-3 Aminohexanoate] or Decorinyl™ [INCI: Tripeptide 10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Xpertmoist™ [INCI: Glycerin, *Pseudoalteromonas* Ferment Extract, Xanthan Gum, Proline, Alanine, Serine, Ethylhexylglycerin, Caprylyl Glycol], Serilesine® [INCI: Hexapeptide-10] or Thermostressine™ [INCI: Acetyl Tetrapeptide-22], marketed by Lipotec, among others, and/or mixtures thereof.

In a particular embodiment, the matrix metalloprotease inhibiting agent is selected, for example and not restricted to, from the group formed by ursolic acid, isoflavones such as genistein, quercetin, carotenoids, lycopene, soy extract, cranberry extract, rosemary extract, extract of *Trifolium pratense* (red clover), extract of *Phormium tenax* (New Zealand flax), kakkon-to extract, sage extract, retinol and its derivatives, retinoic acid and its derivatives, sapogenins such as diosgenin, hecogenin, smilagenin, sarsapogenin, tigogenin, yamogenin and yucagenin, among others, Collalift® [INCI: Hydrolyzed Malt Extract], Juvenesce [INCI: Ethoxydiglicol and Caprylic Triglyceride, Retinol, Ursolic Acid, Phytonadione, Ilomastat] or EquiStat [INCI: *Pyrus Malus* Fruit Extract, *Glycine Soja* Seed Extract] marketed by Coletica/Engelhard/BASF, Pepha®-Timp [INCI: Human Oligopeptide-20], Regu-Age [INCI: Hydrolyzed Rice Bran Protein, *Glycine Soja* Protein, Oxido Reductases] or Colhibin [INCI: Hydrolyzed Rice Protein] marketed by Pentapharm/DSM, Lipeptide [INCI: Hydrolized Vegetable Protein] or Peptide AC29 [INCI: Acetyl Tripeptide-30 Citrulline] marketed by Lipotec, Litchiderm™ [INCI: *Litchi Chinensis* Pericarp Extract] or Arganyl™[INCI: *Argania Spinosa* Leaf Extract] marketed by Laboratories Sérobiologiques/Cognis/BASF, MDI Complex® [INCI: Glycosaminoglycans] or ECM-Protect® [INCI: Water (Aqua), Dextran, Tripeptide-2] marketed by Atrium Biotechnologies/Unipex Innovations, Dakaline [INCI: *Prunus Amygdalus Dulcis, Anogeissus Leiocarpus* Bark Extract] marketed by Soliance, Homeostatine [INCI: *Enteromorpha Compressa, Caesalpinia Spinosa*] marketed by Provital, Timp-Peptide [proposed INCI: Acetyl Hexapeptide] or ECM Moduline [proposed INCI: Palmitoyl Tripeptide] marketed by Infinitec Activos, IP2000 [INCI: Dextran, Trifluoroacetyl Tripeptide-2] marketed by Institut Europeen de Biologie Cellulaire/Unipex Innovations, Actimp 1.9.3® [INCI: Hydrolyzed Lupine Protein] marketed by Expanscience Laboratories, Vitaderm® [INCI: Alcohol, Water (Aqua), Glycerin, Hydrolyzed Rice Protein, *Ilex Aquifolium* Extract, Sodium Ursolate, Sodium Oleanolate] marketed by Rahn, adapalene, tetracyclines and their derivatives such as minocycline, rolitetracycline, chlortetracycline, metacycline, oxytetracycline, doxycycline, demeclocycline and their salts, Batimastat [BB94; [4-(N-hydroxyamino)-2R-isobutyl-3S-(thiophene-2-ilthymethyl)succinyl]-L-phenylalanine-N-methylamide], Marimastat [BB2516; [2S—[N-4(R*),2R*,3S]]-N-4[2,2-dimethyl-1-[methylaminocarbonyl]propyl]-N1,2-dyhydroxy-3-(2-methyl-propyl) butanediamide], among others.

In a particular embodiment, the firming and/or redensifying and/or restructuring agent is selected, for example and not restricted to, from the group formed by extracts of *Malpighia punicitolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: *Triticum Vulgare, Silybum Marianum, Glycine Soy, Equisetum Arvense, Alchemilla Vulgaris, Medicago*

*Sativa, Raphanus Sativus*] or Polyplant® Refirming [INCI: Coneflower, Asiatic *Centella*, Fucus, Fenugreek] marketed by Provital, Lanablue® [INCI: Sorbitol, *Algae* Extract] marketed by Atrium Biotechnologies/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, *Aratostaphylos Uva Ursi* Leaf Extract], Cytokinol® LS [INCI: Hydrolyzed Casein, Hydrolyzed Yeast Protein, Lysine HCl] or Firmiderm® LS9120 [INCI: *Terminalia Catappa* Leaf Extract, *Sambucus Negra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Silusyne™[INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Adifyline™[INCI: Acetyl Hexapeptide-38] marketed by Lipotec, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, *Sclerotium* Gum] marketed by Atrium Biotechnologies/Unipex Innovations or IP2000 [INCI: Dextran, Trifluoroacetyl Tripeptide-2] marketed by Institut Europeen de Biologie Cellulaire/Unipex Innovations, among others.

In a particular embodiment, the anti-itching agent is selected for example, and not restricted to, from the group formed by extracts of *Abelmoschus esculentus, Actaea alba, Aglaia odorata, Alkanna tinctoria, Althaea officinalis, Altingia excelsa, Andropogon virginicus, Aralia nudicaulis, Aralia racemosa, Argemone mexicana, Barleria prionitis, Camelia sinensis, Caesalpinia digyna, Campsis grandiflora, Carissa congesta, Carthamus oxyacantha, Cassia tora, Chrysanthemum indicum, Cimicifuga racemosa, Cinnamomum camphora, Clematis vitalba, Cuscuta reflexa, Diospyros peregrina, Enicostema axillare, Hammamelis virginiana, Jatropha multifida, Lavandula officinalis, Lavandula latifolia, Liquidambar orientalis, Lithospermum officinale, Madhuca longifolia, Martynia annua, Medicago sativa, Michelia champaca, Mikania glomerata, Mimosa pudica, Oryza sativa, Phaseolus vulgaris, Phyllanthus urinaria, Phyllanthus virgatus, Pistacia vera, Polygonum hydropiper, Quercus ilex, Rauvolfia caffra, Ricinus communis, Rubus idaeus, Sagittaria sagittifolia, Sandoricum koetjape, Sapindus mukorossi, Schleichera oleosa, Sesbania grandiflora, Spondias dulcis, Tilia sp., Toona ciliata, Tragia involucrata, Trichosanthes quinquangulata, Vaccaria pyramidata, Ventilago madraspatana, Veratrum album* or *Xanthium strumarium* among others or a synthetic compound or product of biotechnological origin which is an anti-itching agent, for example and not restricted to, Neutrazen™ [INCI: Water, Butylene Glycol, Dextran, Palmitoyl Tripeptide-8] marketed by Atrium/Unipex Innovations, Meliprene® [INCI: Dextran, Acetil Heptapeptide-1] marketed by Institut Européen de Biologie Cellulaire/Unipex Innovations, Delisens™ [proposed INCI: Acetyl Hexapeptide-46] marketed by Lipotec/Lubrizol, Skinasensyl™ [INCI: Acetyl Tetrapeptide-15] marketed by Laboratoires Sérobiologiques/Cognis/BASF, SymSitive® 1609 [INCI: 4-t-Butylcyclohexanol] marketed by Symrise, Symbiocell™ [INCI: Extract from *Cestrum Latifolium*] marketed by BASF, Gatuline® Derma-Sensitive [INCI: Octyldodecyl Myristate, *Capparis Spinosa* Fruit Extract] marketed by Gattefoss6 or MAXnolia [INCI: *Magnolia Officinalis* Bark Extract, *Vitis Vinifera/Vitis Vinifera* (Grape) Seed Extract, Tocopherol] marketed by Mibelle Biochemistry among others, or mixtures thereof.

In another particular embodiment, then anti-inflammatory agent is selected, for example and not restricted to, from the group formed by extract of madecassoside, extract of *echinacea*, amaranth seed oil, sandal wood oil, extract of peach tree leaf, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, omega-3 and omega-6 fatty acids, Neutrazen™ [INCI: Water, Butylene Glycol, Dextran, Palmitoyl Tripeptide-8] marketed by Atrium Innovations/Unipex Group, Meliprene® [INCI: Dextran, Acetyl Heptapeptide-1] marketed by Institut Européen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Sérobiologiques/Cognis, Calmosensine™[INCI: Acetyl Dipeptide-1] marketed by Sederma, coenzyme Q10 or alkyl glyceryl ethers.

In another particular embodiment, the free radical scavenger agent and/or agents against atmospheric pollution, reactive carbonyl or oxygen species scavengers and/or anti-glycation agent is selected, for example and not restricted to, from the group formed by carnosine and its derivatives, GHK [INCI: Tripeptide-1] and its salts and/or derivatives, or Aldenine® [INCI: Hydrolized Wheat Protein, Hydrolized Soy Protein, Tripeptide-1], Preventhelia™ [INCI: Diaminopropionoyl Tripeptide-33], Lipochroman™ 6 [INCI: Dimethylmethoxy Chromanol], dGlyage™ [INCI: Lysine HCl, Lecithin, Tripeptide-9 Citrulline] and Vilastene™ [INCI: Lysine HCl, Lecithin, Tripeptide 10 Citrulline] marketed by Lipotec.

In another particular embodiment, the inhibitor of neuronal exocytosis, anticholinergic agent, agent inhibiting acetylcholine receptor clustering and/or a muscle contraction inhibiting agent is selected, for example and not restricted to, from the group formed by extracts of *Atropa belladonna, Hyoscyamus niger, Mandragora officinarum, Chondodendron tomentosum*, plants from the *Brugmansias* genus, or from the *Daturas* genus, *Clostridium botulinum* toxin, peptides derived from the protein SNAP-25, peptides derived from the protein synaptotagmin, peptides derived from the protein syntaxin, peptides derived from the protein synaptobrevin, peptides derived from the protein snapin, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI:

Pentapeptide-18] or Inyline™ [INCI: Acetyl Hexapeptide-30] marketed by Lipotec/Lubrizol, BONT-L-Peptide [INCI: Palmitoyl Hexapeptide-19] marketed by Infinitec Activos, and Vialox® [INCI: Pentapeptide-3] or Syn® Ake® [INCI: Dipeptide Diaminobutyroyl Benzylamide Diacetate] marketed by Pentapharm/DSM among others, or mixtures thereof.

In another particular embodiment, the body odor absorbent agent and/or body odor masking agent, deodorant and/or antiperspirant agent and/or perfume is selected, for example and not restricted to, from the group formed by the complex zinc salt of ricinoleic acid, derived from abiotic acid, salvia essence, chamomile essence, carnation essence, lemon balm essence, mint essence, cinnamon leaf essence, lime blossom essence, juniper berry essence, vetiver essence, frankincense essence, galbanum essence, labdanum essence, lavender essence, peppermint essence, benzoin, bergamot, dihydromyrcenol, lilial, lyral, citronellol, lemon essence, mandarin essence, orange essence, lavender essence, muscatel, geranium bourbon essence, aniseed, cilantro, cumin, juniper, extracts of fleur-de-lis, lily, roses, jasmine, neroli; benzyl acetate, p-tert-butylcyclohexyl acetate, linalyl acetate, phenylethyl acetate, ethylmethylphenyl glycinate, linalyl benzoate, benzyl formiate, alylcyclohexyl propionate, stiralyl propionate, benzyl salicylate, benzylethylether, linear alkanes with from 8 to 18 carbon atoms, citral, ricinoleic acid, citronellal, citronellyl oxyacetaldehyde, cyclamen aldehyde, hydroxycitronellal, bourgeonal, ionones, methyl cedryl ketone, anethole, eugenol, isoeugenol, geraniol, linalool, terpineol, phenylethylalcohol, α-hexylcinnamaldehyde, geraniol, benzylacetone, cyclamenaldehyde, ambroxan, indole, hedione, sandelice, cyclovertal, β-damascone, allyl amyl glycolate, dihydromyrcenol, phenoxyethyl isobutyrate, cyclohexyl salicylate, phenylacetic acid, geranyl acetate, romilate, irotyl, floramate, aluminum salts such as alum, aluminum chloride, aluminum chlorohydrate, aluminum dichlorohydrate, aluminum sesquichlorohydrate, aluminum hydroxy allantoinate, aluminum chlorotartrate, aluminum and zirconium trichlorohydrate, aluminum and zirconium tetrachlorohydrate, aluminum and zirconium pentachlorohydrate and/or mixtures thereof, Leuphasyl® [INCI: Pentapeptide-18], SNAP-7 [INCI: Acetyl Heptapeptide-4], SNAP-8 [INCI: Acetyl Octapeptide-3], Argireline® [INCI: Acetyl Hexapeptide-8] or Inyline™ [INCI: Acetyl Hexapeptide-30] marketed by Lipotec/Lubrizol, Vialox® [INCI: Pentapeptide 3] or Syn® Ake® [INCI: Dipeptide Diaminobutyroyl Benzylamide Diacetate] marketed by Pentapharm/DSM and BONT-L-Peptide [INCI: Palmitoyl Hexapeptide-19] marketed by Infinitec Activos among others, or mixtures thereof.

Applications

A third aspect of this invention refers to the use of the exopolysaccharide of the strain of the species *Vibrio* sp. with deposit number CNCM I-4277, in the preparation of a cosmetic or dermopharmaceutical composition for the treatment and/or care of the skin, mucous membranes, hair and/or nails.

In another particular embodiment, this invention refers to the use of the exopolysaccharide of the strain of the species *Vibrio* sp. with deposit number CNCM I-4277, in the preparation of a cosmetic or dermopharmaceutical composition for the treatment and/or prevention of aging.

In another particular embodiment, this invention refers to the use of the exopolysaccharide of the strain of the species *Vibrio* sp. with deposit number CNCM I-4277, in the preparation of a cosmetic or dermopharmaceutical composition for the treatment and/or prevention of wrinkles on the skin, and is preferably a wrinkle filling treatment or is a treatment and/or prevention of expression wrinkles.

In another particular embodiment, this invention refers to the use of the exopolysaccharide of the strain of the species *Vibrio* sp. with deposit number CNCM I-4277 in the preparation of a cosmetic or dermopharmaceutical composition for the stimulation of hyaluronic acid synthesis.

In another particular embodiment, this invention refers to the use of the exopolysaccharide of the strain of the species *Vibrio* sp. with deposit number CNCM I-4277 in the preparation of a cosmetic or dermopharmaceutical composition for the inhibition of neuronal exocytosis.

In another particular embodiment, this invention refers to the use of the exopolysaccharide of the strain of the species *Vibrio* sp. with deposit number CNCM I-4277 in the preparation of a cosmetic or dermopharmaceutical composition for the treatment and/or care of conditions, disorders and/or diseases which are a result of a lack or decrease in hydration of the skin, mucous membranes, hair and/or nails. Preferably the conditions, disorders and/or diseases are selected from the group formed by dry skin, xerosis, hyperkeratosis, reactive hyperkeratosis, palmar and plantar hyperkeratosis, corns and calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, couperose, vaginal dryness, ocular dryness, dry hair, brittle hair and nails.

In another particular embodiment, this invention refers to the use of the exopolysaccharide of the strain of the species *Vibrio* sp. with deposit number CNCM I-4277 in the preparation of a cosmetic or dermopharmaceutical composition for the treatment and/or care of conditions, disorders and/or diseases which are a result of inflammation of the skin, mucous membranes and/or nails. Preferably the conditions, disorders and/or diseases are selected from the group formed by sensitive skin, dermatitis, atopic dermatitis, contact dermatitis, diaper dermatitis, seborrheic dermatitis, eczema, hyperproliferative skin disease, burns, sunburn, paronychia, inflammation of the mucous membrane of the vagina, inflammation of the oral mucous membranes, gingivitis, periodontitis.

In another particular embodiment, this invention refers to the use of the exopolysaccharide of the strain of the species *Vibrio* sp. with deposit number CNCM I-4277 in the preparation of a cosmetic or dermopharmaceutical composition for the healing of the skin and/or reepithelization.

In another particular embodiment, this invention refers to the use of the exopolysaccharide of the strain of the species *Vibrio* sp. with deposit number CNCM I-4277 in the preparation of a cosmetic or dermopharmaceutical composition for the treatment and/or prevention of pain of the skin, mucous membranes and/or nails. Preferably, the pain is selected from pain associated with conditions, diseases and/or disorders, for example and not restricted to, touch sensitivity, sensitivity to cold, sensitivity to heat, cutaneous irritation, post-hair removal cutaneous irritation, post-shaving cutaneous irritation, psoriasis, sensitive skin, dermatitis, atopic dermatitis, contact dermatitis, diaper dermatitis, seborrheic dermatitis, eczema, lichen planus, burns, sunburn, arthritis, rheumatoid arthritis, osteoarthritis, psoriatic arthritis, hypersensitivity, cutaneous pain or irritation after surgery, after intense pulsed light treatment (IPL), after treatment with monochromatic pulsed light (laser), after a treatment with chemical desquamating agents or after overexposure to external aggressive agents, among others.

In another particular embodiment, this invention refers to the use of the exopolysaccharide of the strain of the species *Vibrio* sp. with deposit number CNCM I-4277 in the preparation of a cosmetic or dermopharmaceutical composition for the treatment and/or prevention of itching of the skin, mucous membranes and/or nails. Preferably, the itching is selected from itching associated with conditions, diseases and/or disorders, for example and not restricted to, dermatitis, atopic dermatitis, contact dermatitis, diaper dermatitis, dermatitis herpetiformis, photodermatosis, photosensitivity, pregnancy related dermatitis, menopause related dermatitis, eczema, sensitive skin, psoriasis, chickenpox, herpes, herpes zoster, Netherton's syndrome, peeling skin syndrome, lichen planus, acne, dandruff, seborrhea, seborrheic dermatitis, alopecia, athlete's foot, candidiasis, hemorrhoids, vaginal itching, perianal itching, anogenital itching, sunburn, hives, pruritic otitis, itchy eyes, senile pruritus, aquagenic pruritus, prurigo nodularis, prurigo planus, pityriasis rosea, xerosis and dry skin, allergic reactions, allergies to medicines, food allergies, allergies to chemical products, exposure to poisonous plants and exposure to insect bites, among others.

In another particular embodiment, this invention refers to the use of the exopolysaccharide of the strain of the species *Vibrio* sp. with deposit number CNCM I-4277 in the preparation of a cosmetic or dermopharmaceutical composition for the treatment and/or prevention of hyperhidrosis.

In another particular embodiment, this invention refers to the use of the exopolysaccharide of the strain of the species *Vibrio* sp. with deposit number CNCM I-4277 in the preparation of a cosmetic or dermopharmaceutical composition for the removal and/or prevention of the formation of free radicals.

In another particular embodiment, this invention refers to the use of the exopolysaccharide of the strain of the species *Vibrio* sp. with deposit number CNCM I-4277 for the treatment and/or prevention of perspiration, treatment and/or care of disorders of the skin selected from the group formed by calluses or warts, treatment stimulating hair growth and/or prevention of hair loss.

Preferably, the treatment and/or prevention of hyperhidrosis or perspiration, is a treatment and/or prevention of axillary, facial, genital, palmar or plantar hyperhidrosis or perspiration.

An additional aspect of this invention refers to a method of treatment and/or care of the skin, mucous membranes, hair and/or nails which comprises the administration of a cosmetically and/or dermopharmaceutically effective quantity of the exopolysaccharide of the strain of the species *Vibrio* sp. with deposit number CNCM I-4277.

In a particular embodiment, this invention refers to a method of treatment and/or prevention of aging and/or photoaging which comprises the administration of a cosmetically and/or dermopharmaceutically effective quantity of the exopolysaccharide of the strain of the species *Vibrio* sp. with deposit number CNCM I-4277.

In another particular embodiment, this invention refers to method of stimulation of hyaluronic acid synthesis which comprises the administration of a cosmetically and/or dermopharmaceutically effective quantity of the exopolysaccharide of the strain of the species *Vibrio* sp. with deposit number CNCM I-4277.

In another particular embodiment, this invention refers to a method of inhibition of neuronal exocytosis which comprises the administration of a cosmetically and/or dermopharmaceutically effective quantity of the exopolysaccharide of the strain of the species *Vibrio* sp. with deposit number CNCM I-4277.

In another particular embodiment, this invention refers to method of treatment and/or prevention of wrinkles on the skin which comprises the administration of a cosmetically and/or dermopharmaceutically effective quantity of the exopolysaccharide of the strain of the species *Vibrio* sp. with deposit number CNCM I-4277, and preferably the treatment is a wrinkle filling treatment or is a treatment and/or prevention of expression wrinkles.

In another particular embodiment, this invention refers to method of treatment and/or care of those conditions, disorders and/or diseases of mammals, preferably of humans, which are a result of a lack or decrease in the hydration of the skin, mucous membranes, hair and/or nails which comprises the administration of a cosmetically and/or dermopharmaceutically effective quantity of the exopolysaccharide of the strain of the species *Vibrio* sp. with deposit number CNCM I-4277. Preferably, the conditions, disorders and/or diseases which are a result of a lack or decrease in the hydration of the skin, mucous membranes, hair and/or nails are selected from the group formed by dry skin, xerosis, hyperkeratosis, reactive hyperkeratosis, palmar and plantar hyperkeratosis, corns and calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, couperose, vaginal dryness, ocular dryness, dry hair, brittle hair and brittle nails.

In another particular embodiment, this invention refers to method of treatment and/or care of those conditions, disorders and/or diseases which are a result of inflammation of the skin, mucous membranes and/or nails which comprises the administration of a cosmetically and/or dermopharmaceutically effective quantity of the exopolysaccharide of the strain of the species *Vibrio* sp. with deposit number CNCM I-4277. Preferably the conditions, disorders and/or diseases are selected from the group formed by sensitive skin, dermatitis, atopic dermatitis, contact dermatitis, diaper dermatitis, seborrheic dermatitis, eczema, hyperproliferative skin disease, burns, sunburn, paronychia, inflammation of the mucous membrane of the vagina, inflammation of the oral mucous membranes, gingivitis, periodontitis.

In another particular embodiment, this invention refers to a method of healing of the skin and/or reepithelization which comprises the administration of a cosmetically and/or dermopharmaceutically effective quantity of the exopolysaccharide of the strain of the species *Vibrio* sp. with deposit number CNCM I-4277.

In another particular embodiment, this invention refers to method of treatment and/or prevention of pain of the skin, mucous membranes and/or nails which comprises the administration of a cosmetically and/or dermopharmaceutically effective quantity of the exopolysaccharide of the strain of the species *Vibrio* sp. with deposit number CNCM I-4277. Preferably, the pain is selected from pain associated with conditions, diseases and/or disorders, for example and not restricted to, touch sensitivity, sensitivity to cold, sensitivity to heat, cutaneous irritation, post-hair removal cutaneous irritation, post-shaving cutaneous irritation, psoriasis, sensitive skin, dermatitis, atopic dermatitis, contact dermatitis, diaper dermatitis, seborrheic dermatitis, eczema, lichen planus, burns, sunburn, arthritis, rheumatoid arthritis, osteoarthritis, psoriatic arthritis, hypersensitivity, cutaneous pain or irritation after surgery, after intense pulsed light treatment (IPL), after treatment with monochromatic pulsed light (laser), after a treatment with chemical desquamating agents or after overexposure to external aggressive agents, among others.

In another particular embodiment, this invention refers to method of treatment and/or prevention of itching of the skin, mucous membranes and/or nails which comprises the administration of a cosmetically and/or dermopharmaceutically effective quantity of the exopolysaccharide of the strain of the species *Vibrio* sp. with deposit number CNCM I-4277. Preferably, the itching is selected from itching associated with conditions, diseases and/or disorders, for example and not restricted to, dermatitis, atopic dermatitis, contact dermatitis, diaper dermatitis, dermatitis herpetiformis, photodermatosis, photosensitivity, pregnancy related dermatitis, menopause related dermatitis, eczema, sensitive skin, psoriasis, chickenpox, herpes, herpes zoster, Netherton's syndrome, peeling skin syndrome, lichen planus, acne, dandruff, seborrhea, seborrheic dermatitis, alopecia, athlete's foot, candidiasis, hemorrhoids, vaginal itching, perianal itching, anogenital itching, sunburn, hives, pruritic otitis, itchy eyes, senile pruritus, aquagenic pruritus, prurigo nodularis, prurigo planus, pityriasis rosea, xerosis and dry skin, allergic reactions, allergies to medicines, food allergies, allergies to chemical products, exposure to poisonous plants and exposure to insect bites, among others.

In another particular embodiment, this invention refers to method of treatment and/or prevention of hyperhidrosis which comprises the administration of a cosmetically and/or dermopharmaceutically effective quantity of the exopolysaccharide of the strain of the species *Vibrio* sp. with deposit number CNCM I-4277.

In another particular embodiment, this invention refers to method of elimination and/or prevention of the formation of free radicals which comprises the administration of a cosmetically and/or dermopharmaceutically effective quantity of the exopolysaccharide produced by the strain of the species *Vibrio* sp. with deposit number CNCM I-4277.

In another particular embodiment, this invention refers to method of treatment and/or prevention of perspiration, treatment and/or care of disorders of the skin selected from the group formed by calluses or warts, treatment stimulating hair growth and/or prevention of hair loss, which comprises the administration of a cosmetically and/or dermopharmaceutically effective quantity of the exopolysaccharide of the strain of the species *Vibrio* sp. with deposit number CNCM I-4277.

Preferably, the treatment and/or prevention of hyperhidrosis or perspiration, is a treatment and/or prevention of axillary, facial, genital, palmar or plantar hyperhidrosis or perspiration.

The frequency of the application or administration in the methods can vary widely, depending on the needs of each subject and severity of the condition, disorder or disease to be treated or cared for, suggesting a range of application or administration from once per month to ten times per day, preferably from once per week to four times per day, more preferably from three times per week to three times per day, even more preferably once or twice per day.

This invention is understood more clearly with the help of the following examples, without limitation and included for illustrative purposes only which describe the preparation and characterization of exopolysaccharides and compositions containing them in accordance with the invention.

EXAMPLES

Example 1

Preparation and Isolation of the Exopolysaccharide Produced by the Strain of the Species *Vibrio* Sp. with Deposit Number CNCM I-4277 a) Method of Culture of the Strain of the Species *Vibrio* Sp. with Deposit Number CNCM I-4277.

The strain of the species *Vibrio* sp with deposit number CNCM I-4277 was cultured in a fermenter, at 29° C. and at a pH of 7.5, whose broth contained 2216E medium (ZoBell C. E. *J. Mar. Res.*, 1941, 4:42.) enriched with glucose (20 g/l). An inoculum was prepared with 10% (v/v) of a pre-culture and the duration of the fermentation was extended to 72 hours. The speed of aeration and stirring was 2 vvm and 250 rpm, respectively.

b) Purification of the Exopolysaccharide.

The bacteria were separated from the broth by centrifugation at 12,000 g for 45 mins. The polysaccharide was filtered with distilled water by ultrafiltration with a polyethersulfone membrane for polysaccharides of over 100 KDa in molecular weight resulting in a polymer with a distribution of molecular weight showing a first peak with a molecular weight of 500,000 Da and a second peak with a molecular weight of 1,000,000 Da. The level of sulfation of the polymer obtained was 3%.

Example 2

Physical-Chemical Characterization of the Exopolysaccharide Produced by the Strain of the Species *Vibrio* Sp. with Deposit Number CNCM I-4277

The content of neutral and acid monosaccharides of the exopolysaccharide obtained according to that described in example 1 was determined by hydrolysis and gas chromatography according to the method described by Kamerling et al. *Biochem. J.*, 1975 151:491-495, and modified by Montreuil et al. in 1986, *Glycoproteins. In Carbohydrate analysis: a practical approach*. Eds Chaplin et Kennedy, I.R.L Press, Oxford, Washington D.C., pp 143-204. The percentual relationship of sugars obtained was 4.11% of fucose, 20.58% of glucose, 28.81% of glucuronic acid and 46.50% of N-acetylglucosamine.

Example 3

Preparation of a Microemulsion of the Exopolysaccharide Produced by the Strain of the Species *Vibrio* Sp. with Deposit Number CNCM I-4277

In a suitable vessel Docusate Sodium USP [INCI: DIETHYLHEXYL SODIUM SULFOSUCCINATE] and isostearic acid [INCI: ISOSTEARIC ACID](phase A) were mixed together. In another vessel the exopolysaccharide produced by the strain of the species *Vibrio* sp. with deposit number CNCM I-4277 was dissolved in ethanol [INCI: ALCOHOL] and water [INCI: WATER (AQUA)] (phase B). Phase B was slowly added to phase A under stirring. See Table 1.

TABLE 1

| | INGREDIENT | % in weight |
|---|---|---|
| A | DIETHYLHEXYL SODIUM SULFOSUCCINATE | 13.46 |
| A | ISOSTEARIC ACID | 76.29 |
| B | EXOPOLYSACCHARIDE OF THE STRAIN CNCM I-4277 | 0.25 |
| B | WATER (AQUA) | 7.00 |
| B | ALCOHOL | 3.00 |

Example 4

Preparation of a Composition of Lipid Nanoparticles Containing the Exopolysaccharide Produced by the Strain of the Species *Vibrio* Sp. with Deposit Number CNCM I-4277

In a suitable vessel the following ingredients were added in this order: water [INCI: WATER (AQUA)], Amigel® [INCI: *SCLEROTIUM* GUM], Zemea™ [INCI: PROPANEDIOL] and phenoxyethanol [INCI: PHENOXYETHANOL] (phase A ingredients), and were stirred until fully homogenized.

In another vessel, the microemulsion of the exopolysaccharide produced by strain CNCM I-4277, prepared according to example 3, IP refined soybean oil Ph. Eur [INCI: *GLYCINE SOJA* (SOYBEAN) OIL], Arlacel 83V [INCI: SORBITAN SESQUIOLEATE], and Arlamol HD [INCI: ISOHEXADECANE] were added (phase B ingredients).

Then, the mixture of ingredients B was added to the mixture of ingredients A, under turbine stirring until an emulsion was formed.

Lastly, the mixture was homogenized under pressure in a microfluidizer for 3 cycles with an entrance pressure of 80 bar and pressure on exit of 15000 psi. Throughout the whole process the temperature of the sample was maintained at 25° C. using a water/glycol refrigeration circuit. The high pressure homogenizations were carried out in a Microfluidics model "M110-Y" microfluidizer. The Ultraturrax stirrer for the formation of microemulsions was the "D-8" model by Miccra RT.

Then, a suspension of Quat Soy LDMA 25 [INCI: LAURYLDIMONIUM HYDROXYPROPYL HYDROLYZED SOY PROTEIN] in water was added dropwise and under stirring (phase C ingredients). See Table 2.

TABLE 2

| | INGREDIENTS | % IN WEIGHT |
|---|---|---|
| A | WATER (AQUA) | q.s.p. 100 |
| A | SCLEROTIUM GUM | 0.50 |
| A | PROPANEDIOL | 5.00 |
| A | PHENOXYETHANOL | 2.6 |
| B | MICROEMULSION OF EXAMPLE 3 | 8.00 |
| B | GLYCINE SOJA (SOYBEAN) OIL | 12.00 |
| B | SORBITAN SESQUIOLEATE | 4.30 |
| B | ISOHEXADECANE | 5.50 |
| C | WATER (AQUA) | 2.00 |
| C | LAURYLDIMONIUM HYDROXYPROPYL HYDROLYZED SOY PROTEIN | 0.20 |

Example 5

Obtaining of a Composition of Coacervation Microcapsules Containing the Exopolysaccharide Produced by the Strain of the Species *Vibrio* Sp. with Deposit Number CNCM I-4277

Carboxymethyl cellulose [INCI: CELLULOSE GUM] was added to water in a suitable vessel (phase A). Gelatin [INCI: GELATIN], water [INCI: WATER (AQUA)], Zemea™ [INCI: 1,3-PROPANEDIOL] and phenoxyethanol [INCI: PHENOXYETHANOL] (phase B) were added in a second vessel maintaining the stirring for 15 minutes, and bringing it to boiling point until total dilution was obtained. The temperature of phase B was lowered in the bath to 75° C. and was added dropwise to phase A.

Avoiding the temperature was under 60° C. and adjusting the pH between 5.0-5.5, the following ingredients were added under stirring: Vitamin E acetate [INCI: TOCOPHERYL ACETATE], microemulsion of exopolysaccharide produced by the bacterial strain CNCM I-427 according to example 3 and soybean oil [INCI: *GLYCINE SOJA* (SOYBEAN) OIL] (phase C). Then, the pH of the mixture was adjusted with citric acid [INCI: CITRIC ACID] (phase D) to 4.42 and was left stirring for 30 minutes, readjusting the pH when necessary. Subsequently, the mixture was left to cool to room temperature readjusting the pH when necessary. Once at room temperature, the pH was increased with NaOH at 7.0-7.5 (phase E)

Finally, glutaraldehyde [INCI: GLUTARAL] dispersed in water [INCI: WATER (AQUA)] (phase F) was added and was left to react for 2 hours. See Table 3.

TABLE 3

| | INGREDIENT | % in weight |
|---|---|---|
| A | CELLULOSE GUM | 0.60 |
| A | WATER (AQUA) | 29.54 |
| B | GELATIN | 0.60 |
| B | WATER (AQUA) | 30.00 |
| B | 1,3-PROPANEDIOL | 4.18 |
| B | PHENOXYETHANOL | 0.84 |
| C | TOCOPHERYL ACETATE | 3.50 |
| C | Microemulsion of Example 3 | 10.00 |
| C | GLYCINE SOJA (SOYBEAN) OIL | 6.50 |
| D | CITRIC ACID | 0.15 |
| D | WATER (AQUA) | 1.00 |
| E | SODIUM HYDROXIDE | 0.06 |
| E | WATER (AQUA) | 0.24 |
| F | GLUTARAL | 0.50 |
| F | WATER (AQUA) | q.s.p. 100 |

Example 6

Obtaining of Microcapsules Containing the Exopolysaccharide Produced by the Strain of the Species *Vibrio* Sp. with Deposit Number CNCM I-4277 Bound to Cationic Polymers of Cocodimonium Methosulfate Luviquat HM552 [INCI: COCOTRIMONIUM METHOSULFATE] was added to the capsules of example 5 under stirring.

TABLE 4

| | INGREDIENT | % in weight |
|---|---|---|
| A | Microcapsules of Example 5 | 60 |
| A | COCOTRIMONIUM METHOSULFATE | 40 |

Example 7

Preparation of a Cosmetic Composition of the Exopolysaccharide Produced by the Strain of the Species *Vibrio* Sp. with Deposit Number CNCM I-4277

Purified water [INCI: WATER (AQUA)], Hydrolyte 5 2/016020 [INCI: PENTYLENE GLYCOL] and Microcare BNA [INCI: BENZYL ALCOHOL] were dissolved in a suitable vessel. This mixture of ingredients was stirred constantly and heated to 70-75° C. Maintaining the temperature at 70-75° C., subsequently Carbopol® 934 [INCI: CARBOMER] was added little by little. This set of ingredients constitutes phase A.

The ingredients from phase B Finsolv-TN [INCI: C12-15 ALKYL BENZOATE], Phytocream 2000 [INCI: GLYCERYL STEARATE, CETEARYL ALCOHOL, POTASSIUM PALMITOYL HYDROLYZED WHEAT PROTEIN], Waglinol 13088 [INCI: ETHYLHEXYL COCOATE], phenoxyethanol [INCI: PHENOXYETHANOL] and Arlatone Map 160 K [INCI: POTASSIUM CETYL PHOSPHATE] were also dissolved at 70-75° C. Once dissolved, they were added little by little, under turbine stirring to the ingredients of the phase mixture.

In another vessel Silicone dc 200 [INCI: DIMETHICONE] and vitamin E acetate [INCI: TOCOPHERYL ACETATE] were added (phase C ingredients). Then the mixture of ingredients from phase C was added to the mixture of ingredients from A and B under turbine stirring at 50° C. A solution at 0.75% of the exopolysaccharide produced by the strain of the species *Vibrio* sp. with deposit number CNCM I-4277 was also prepared together with Disodium hydrogen Phosphate [INCI: DISODIUM PHOSPHATE], Sodium Phosphate 2-Hydrate [INCI: SODIUM PHOSPHATE], Dermosoft Pea Eco [INCI: PHENETHYL ALCOHOL] and Dermosoft GMCY [INCI: GLYCERYL CAPRYLATE] (phase C1 ingredients), which were subsequently added to the resulting emulsion of the mixture of phases A, B and C.

Sepigel™ 305 [INCI: WATER (AQUA), POLYACRYLAMIDE, C13-14 ISOPARAFFIN, LAURETH-7] (phase D) was added under turbine stirring to the emulsion resulting from the mixture of the different phases. The pH was adjusted to 6.0-6.5 by dropwise addition under stirring of sodium hydroxide [INCI: SODIUM HYDROXIDE] (phase E)

Finally, Perfume Ocean 12720 [INCI: FRAGRANCE (PARFUM)] was added to the mixture obtaining a cosmetic composition with the proportions shown in table 5 (phase F).

TABLE 5

| | INGREDIENT | % in weight |
|---|---|---|
| A | WATER (AQUA) | 75.92 |
| A | PENTYLENE GLYCOL | 4.93 |
| A | BENZYL ALCOHOL | 0.99 |
| A | CARBOMER | 0.49 |
| B | C12-15 ALKYL BENZOATE | 4.93 |
| B | GLYCERYL STEARATE | 2.03 |
| B | CETEARYL ALCOHOL | 2.03 |
| B | POTASSIUM PALMITOYL HYDROLYZED WHEAT PROTEIN | 0.86 |
| B | ETHYLHEXYL COCOATE | 2.46 |
| B | PHENOXYETHANOL | 0.89 |
| B | POTASSIUM CETYL PHOSPHATE | 0.49 |
| C | DIMETHICONE | 0.99 |
| C | TOCOPHERYL ACETATE | 0.49 |
| C1 | Exopolysaccharide of the strain CNCM I-4277 | 0.01 |
| C1 | DISODIUM PHOSPHATE | 0.02 |
| C1 | SODIUM PHOSPHATE | 0.01 |
| C1 | PHENETHYL ALCOHOL | 0.01 |
| C1 | GLYCERYL CAPRYLATE | 0.01 |
| D | WATER (AQUA) | 0.34 |
| D | POLYACRYLAMIDE | 0.40 |
| D | C13-14 ISOPARAFFIN | 0.20 |
| D | LAURETH-7 | 0.06 |
| E | SODIUM HYDROXIDE 20% | q.s. |
| F | FRAGRANCE (PARFUM) | 0.10 |

Example 8

Obtaining of Liposomes Containing the Exopolysaccharide Produced by the Strain of the Species *Vibrio* Sp. with Deposit Number CNCM I-4277

The exopolysaccharide obtained according to example 1 was added to water [INCI: WATER (AQUA)] with sodium salicylate [INCI: SODIUM SALICYLATE] in a suitable vessel and phase A was obtained. Water, Zemea™ [INCI: PROPANEDIOL] and phenoxyethanol [INCI: PHENOXYETHANOL] (phases B to D) were added to this phase. When all the previous components were dissolved Leciflor 100 IP [INCI: LECITHIN](phase E) was added little by little under intense stirring until it was completely dissolved. Afterwards Labrasol [INCI: PEG-8 CAPRYLIC/CAPRIC GLYCERIDES] (phase F) was added and left stirring for 10-15 minutes in order to form an emulsion.

TABLE 6

| | INGREDIENT | % in weight |
|---|---|---|
| A | WATER (AQUA) | 6 |
| A | SODIUM SALICYLATE | 0.03 |
| A | Exopolysaccharide of the strain CNCM I-4277 | 1.5 |
| B | WATER (AQUA) | q.s.p. 100 |
| C | PROPANEDIOL | 8.50 |
| D | PHENOXYETHANOL | 1.70 |
| E | LECITHIN | 10.00 |
| F | PEG-8 CAPRYLIC/CAPRIC GLYCERIDES | 4.00 |

The sample was homogenized at high pressure in a microfluidizer for one cycle at an entrance pressure of 80 bar and exit pressure of 12500 psi.

Example 9

Obtaining of Liposomes Containing the Exopolysaccharide Produced by the Strain of the Species *Vibrio* Sp. with Deposit Number CNCM I-4277 Bound to Polyquaternium-16 Cationic Polymers The exopolysaccharide obtained according to example 1 was added to water [INCI: WATER (AQUA)] with sodium salicylate [INCI: SODIUM SALICYLATE] in a suitable vessel and phase A was obtained. Water, Zemea™ [INCI: PROPANEDIOL] and phenoxyethanol [INCI: PHENOXYETHANOL] (phases B a D) were added to this phase. When all the previous components were dissolved Leciflor 100 IP [INCI: LECITHIN] (phase E) was added little by little under intense stirring until it was completely dissolved. Afterwards Labrasol [INCI: PEG-8 CAPRYLIC/CAPRIC GLYCERIDES] (phase F) was added and was left stirring for 10-15 minutes in order to form an emulsion.

TABLE 7

| | INGREDIENT | % in weight |
|---|---|---|
| A | WATER (AQUA) | 6 |
| A | SODIUM SALICYLATE | 0.03 |
| A | Exopolysaccharide of the strain CNCM I-4277 | 1.5 |
| B | WATER (AQUA) | q.s.p. 100 |

TABLE 7-continued

| | INGREDIENT | % in weight |
|---|---|---|
| C | PROPANEDIOL | 8.50 |
| D | PHENOXYETHANOL | 1.70 |
| E | LECITHIN | 10.00 |
| F | PEG-8 CAPRYLIC/CAPRIC GLYCERIDES | 4.00 |

The sample was homogenized at high pressure in a microfluidizer for one cycle at an entrance pressure of 80 bar and 12500 psi on exit. The liposomes obtained were added to Luviquat® HM 552 [INCI: POLYQUATERNIUM-16] in a liposomes:cationic polymer ratio of 1.5:1 under soft stirring.

Example 10

Obtaining of Microcapsules Containing the Exopolysaccharide Produced by the Strain of the Species *Vibrio* Sp. with Deposit Number CNCM I-4277 and Vitamin E Acetate Cationized with Polyquaternium-16

The microcapsules of this example were prepared in the same way as the microcapsules obtained in example 6 according to example 5, but with different concentrations.

TABLE 8

| | INGREDIENT | % in weight |
|---|---|---|
| A | GELATIN | 2.4 |
| A | PHENOXYETHANOL | 0.84 |
| A | 1,3-PROPANEDIOL | 4.175 |
| A | WATER (AQUA) | q.s.p. 100 |
| B | CELLULOSE GUM | 0.6 |
| B | WATER (AQUA) | 30 |
| C | Microemulsion of Example 3 | 0.01 |
| C | TOCOPHERYL ACETATE | 3.50 |
| C | GLYCINE SOJA (SOYBEAN) OIL | 6.50 |
| D | CITRIC ACID | 0.15 |
| D | WATER (AQUA) | 1.00 |
| E | SODIUM HYDROXIDE | 0.10 |
| E | WATER (AQUA) | 10.00 |
| F | GLUTARAL | 0.50 |
| E | WATER (AQUA) | 0.50 |
| G | POLYQUATERNIUM-16 | 15.0 |

Example 11

Study of Hyaluronic Acid Stimulation in Dermal Fibroblasts by the Exopolysaccharide Produced by the Strain of the Species *Vibrio* Sp. with Deposit Number CNCM I-4277

This example studied the hyaluronic acid stimulation by the exopolysaccharide produced by the strain of the species *Vibrio* sp. with deposit number CNCM I-4277.

Human dermal fibroblasts were treated with trypsin and seeded ($3 \times 10^4$ cells/well, in 24-well plates) and incubated for 24 hours in Dulbecco's Modified Eagle Medium (DMEM) with 10% Fetal Bovine Serum (FBS), at 37° C. in air with 5% $CO_2$.

After the incubation, the culture medium was changed for a medium low in serum (DMEM with 0.1% FBS) and were incubated for another 24 hours at 37° C. in air with 5% $CO_2$. Then, the exopolysaccharide produced by the strain of the species *Vibrio* sp. with deposit number CNCM I-4277 was added to the culture medium diluted to a final concentration of 1 mg/mL and it was incubated for additional 48 hours at 37° C. in air with 5% $CO_2$. After the incubation period, the supernatant was collected from each well, and the levels of hyaluronic acid were determined by ELISA immunoassay (Hyaluronan Enzyme-Linked Immunosorbent Assay Kit, K-1200, Echelon), by which the quantity of hyaluronic acid produced in the supernatant of said cultures was determined. 50 ng/ml of PDGF (platelet-derived growth factor) were used as a positive control and untreated cells were used as a negative control. To deduct the values that did not correspond to hyaluronic acid stimulation but to the recognition of the product tested by the antibody of the immunoassay, blank assays with medium plus the tested product but without cells were made.

TABLE 9

| Product | Concentration | Stimulation versus negative control (%) | % N-acetyl glucosemine | % Glucuronic acid | % Components of hyaluronic acid |
|---|---|---|---|---|---|
| CNCM I-4277 | 1 mg/mL | 66.69 | 46.50 | 28.81 | 75.31 |
| Hyactive | 1 mg/mL | 0.97 | 50 | 50 | 100 |
| Positive control | 50 ng/mL | 233.5 | 50 | 50 | 100 |
| Negative control | 0 | 0 | 0 | 0 | 0 |

The quantity of hyaluronic acid stimulated by the exopolysaccharide of this invention, obtained from the bacterial strain CNCM I-4277 was 66.69%.

Example 12

In Vivo Study of Reduction of Wrinkles on the Skin

An in vivo study was carried out of the effectiveness of the reduction of nasogenian wrinkles of the cosmetic composition of example 7.

Nineteen volunteers between 44-56 years old participated in the study. They were included in the Fitzpatrick phototype groups II and III, and shown nasogenian wrinkles of a moderate intensity. The cosmetic composition from example 7 was applied to the volunteers, for 28 days, twice a day on one half of the face.

The effectiveness in the reduction of the nasogenian wrinkles was quantitively evaluated by instrumental measurements of physical parameters (volume, circumference, area and depth) related to the topography of the skin comparing it before the treatment, after 14 and after 28 days. The technique used for the instrumental measurements was Fast Optical In Vivo Topometry of human Skin (FOITS).

The statistical analysis of the evolution of the parameters measured during the study was carried out by means of the Student test, establishing the statistical significance threshold at 5%.

The results obtained from the treatment of the images, the average variations of each parameter with regard to the values at zero time for the 19 volunteers is shown in table 10.

TABLE 10

| | Variation compared to day 0 | |
|---|---|---|
| | Day 14 | Day 28 |
| Volume | −15.39% | −27.05% |
| Circumference | −1.90% | −15.30% |
| Surface area | −6.68% | −17.20% |
| Maximum depth | −13.65% | −19.60% |
| Average depth | −14.72% | −18.54% |

The results from table 10 show a statistically significant improvement in the maximum depth of the nasogenian wrinkles after the cosmetic composition from example 7 was applied, by 13.65% after 14 days and by 19.6% after 28 days. The maximum individual reductions were 64.73% after 14 days and 70.62% after 28 days.

The results from table 10 also show a statistically significant decrease in the average depth of the nasogenian wrinkles once the cosmetic composition from example 7 was applied, by 14.72% after 14 days and by 18.54% after 28 days. The maximum decrease in a volunteer was 65.84% on day 14 and 71.43% on day 28.

The table also shows that after 14 days applying the composition of example 7, the average volume of the nasogenian wrinkles decreased (15.39%), the surface area (6.68%) and the circumference (1.9%), decreasing even more after the 28 days of application. The maximum improvements in an individual at the end of the treatment were 93.48% in volume, 77.84% in the surface area and 79.29% in circumference.

Example 13

Study of the Inhibition of the SNARE Complex Formation with Detection of the Complex by ELISA With the aim of determining the capacity of inhibition of the SNARE complex formation by the exopolysaccharide of the invention, the competitive inhibition of the compounds compared to SNAP-25 was studied with regards to the formation of this complex. The proportion of SNARE complex formed was determined by the ELISA technique, using one of the proteins from the complex bound to GST.

In a 96-well plate VAMP was immobilized (using a 0.037 µM solution) and subsequently the free spaces were blocked with BSA (3%). Parallel to this process, SNAP-25 bound to GST (0.0185 µM), syntaxin (0.037 µM) and the exopolysaccharide produced by the strain of the species *Vibrio* sp. with deposit number CNCM I-4277 (at 1, 0.5 and 0.1 mg/mL) were incubated for 1 hour. The same dilution generated due to the test products addition was generated for the negative complex inhibition control with ultrapure water (18.2 mΩ).

After incubation, the samples were transferred to the plate with immobilized VAMP and were incubated for 1 hour to allow the formation of the SNARE complex. Afterwards, the plate was washed and the complex was detected by a primary antibody anti-GST (Antibody anti-GST epitope TAG, Fisher Cat. no:PA1-982A). The reading was carried out at a wavelength of 490 nm in a TECAN GENios spectrophotometric reader.

Table 11 shows the results of the competitive inhibition of the formation of the SNARE complex by the exopolysaccharide of the invention versus SNAP-25. The percentage of inhibition of the formation of the complex is inversely proportional to the quantity of SNARE complex spectrophotometrically detected.

TABLE 11

| | % inhibition formation SNARE complex | | |
|---|---|---|---|
| | Concentration | | |
| | 1 mg/mL | 0.5 mg/mL | 0.1 mg/mL |
| Expolysaccharide of strain CNCM I-4277 | 46 | 37 | 14 |

Example 14

Study of the Inhibition of the SNARE Complex Formation with Detection of the Complex by Electrophoresis VAMP (6 µM), syntaxin (6 µM) and the exopolysaccharide produced by the strain of the species *Vibrio* sp. with deposit number CNCM I-4277 (at 1 mg/mL, and 0.1 mg/mL) were incubated for 3 hours. The same dilution generated due to the test products addition was generated for the negative complex inhibition control with ultrapure water (18.2 mΩ). Subsequently, SNAP-25 (0.6 µM) was added and the mixture was incubated for an additional 15 hours to allow the formation of the SNARE complex. After incubation, the loading buffer (Laemli Simple Buffer) was added and the mixture was analyzed by 10% acrylamide SDS-PAGE in gel. The amount of complex was determined by an image acquisition and analysis software.

Table 12 shows the results of the inhibition of the formation of the SNARE complex. The percentage of inhibition of the formation of the complex is inversely proportional to the quantity of SNARE complex detected.

TABLE 12

| | % inhibition formation SNARE complex | |
|---|---|---|
| | Concentration | |
| | 1 mg/mL | 0.1 mg/mL |
| Expolysaccharide of strain CNCM I-4277 | 37 | 9 |

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method of treatment of aging and/or photoaging of the skin which comprises the administration, to the skin, of a cosmetically or dermopharmaceutically effective quantity of the exopolysaccharide of the strain of the species *Vibrio* sp. with deposit number CNCM I-4277.

2. The method according to claim 1, wherein the treatment of the aging is a treatment of wrinkles on the skin.

3. The method according to claim 1, wherein the treatment stimulates hyaluronic acid synthesis.

4. The method according to claim 1, wherein the treatment of aging and/or photoaging is a treatment and/or care of a disorder, condition and/or disease which are a consequence of a lack of or decrease in hydration of the skin.

5. The method according to claim 4, wherein the condition, disorder and/or disease is selected from the group consisting of dry skin, xerosis, and combinations thereof.

6. The method according to claim 1, wherein the treatment of aging and/or photoaging is a treatment for eliminating formation of free radicals.

7. The method according to claim 1, wherein the exopolysaccharide has a molecular weight between 100,000 and 10 million Da.

8. The method according to claim 1, wherein the exopolysaccharide includes up to 7% of sulfates.

9. The method according to claim 1, wherein the exopolysaccharide has a chemical modification selected from the group consisting of phosphorylation, sulfonation, acylation, esterification, formation of metallic complexes of the exopolysaccharide, chemical sulfation greater than 7%, and combinations thereof.

10. The method according to claim 1, wherein the exopolysaccharide comprises at least three different neutral monosaccharides and one acid monosaccharide.

11. The method according to claim 10, wherein the neutral monosaccharides are fucose, glucose and N-acetylglucosamine.

12. The method according to claim 10, wherein the acid monosaccharide is glucuronic acid.

13. The method according to claim 10, wherein the exopolysaccharide is a composition, by weight, of 1% to 12% fucose, 10% to 35% glucose, 18% to 40% glucuronic acid, and 34% to 56% N-acetylglucosamine, with the condition that a sum of the percentages does not exceed 100%.

14. A method of inhibition of neuronal exocytosis which comprises the administration, to the skin, of a cosmetically and/or dermopharmaceutically effective quantity of the exopolysaccharide of the strain of the species *Vibrio* sp. with deposit number CNCM I-4277.

15. The method according to claim 1, wherein the exopolysaccharide is administered to the skin in a composition which comprises between 0.00000001% in weight and 20% in weight of the composition.

16. A cosmetic or dermopharmaceutical composition comprising an effective cosmetic or dermopharmaceutical quantity of the exopolysaccharide of the strain of the species *Vibrio* sp. with deposit number CNCM I-4277, and at least one cosmetically or dermopharmaceutically acceptable excipient, adjuvant and/or ingredient.

17. The cosmetic or dermopharmaceutical composition according to claim 16, wherein the exopolysaccharide is incorporated into a cosmetically or dermopharmaceutically acceptable delivery system or sustained release system selected from the group consisting of liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules, nanocapsules, microemulsions and nanoemulsions.

18. The cosmetic or dermopharmaceutical composition according to claim 16, wherein the composition is absorbed on a solid organic polymer or solid mineral support selected from the group consisting of talc, bentonite, silica, starch and maltodextrin.

19. The cosmetic or dermopharmaceutical composition according to claim 16, wherein the composition is incorporated into a fabric, non-woven fabric or medical device.

20. The cosmetic or dermopharmaceutical composition according to claim 16, wherein the composition is present in a formulation selected from the group consisting of multiple emulsions, solutions, liquid crystals, anhydrous compositions, aqueous dispersions, oils, milks, balsams, foams, aqueous or oily lotions, aqueous or oily gels, creams, solutions, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils, sprays or aerosols or in a formulation for oral administration which is selected from the group formed by capsules, gelatin capsules, soft capsules, hard capsules, tablets, powders, granules, chewing gums, solutions, suspensions, emulsions, syrups, polysaccharide films, jellies and gelatins.

21. The cosmetic or dermopharmaceutical composition according to claim 16, wherein the excipient, adjuvant and/or ingredient is selected from the group consisting of hyaluronic acid synthesis-stimulating agents, glycosaminoglycan synthesis-stimulating agents, collagen synthesis-stimulating agents, agents stimulating the synthesis of dermal or epidermal macromolecules and/or capable of inhibiting their degradation, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, heat shock proteins, HSP70 synthesis-stimulating agents, heat shock protein synthesis-stimulating agents, fibronectin synthesis-stimulating agents, sirtuin synthesis-stimulating agents, sirtuin activating agents, agents stimulating the synthesis of lipids and components of the stratum corneum, ceramides, fatty acids, agents that inhibit collagen degradation, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents inhibiting acetylcholinesterase, skin relaxant agents, agents modulating AQP-3, agents modulating aquaporin synthesis, proteins from the aquaporin family, agents modulating PGC-1α synthesis, agents modulating PPARγ activity, agents that increase or reduce the triglyceride content of adipocytes, agents stimulating or delaying adipocyte differentiation, lipolytic agents or agents stimulating lipolysis, anti-cellulite agents, adipogenic agents, agents inhibiting acetylcholine receptor clustering, muscle contraction inhibiting agents, inhibitors of neuronal exocytosis, anti-wrinkle and/or antiaging agents, anticholinergic agents, elastase inhibiting agents, matrix metalloprotease inhibiting agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl or oxygen species scavengers, anti-glycation agents, antihistamine agents, antiviral agents, antiparasitic agents, emulsifiers, emollients, organic solvents, liquid propellants, skin conditioners, humectants, moisture retaining substances, alpha hydroxyacids, beta hydroxyacids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat bags under the eyes, exfoliating agents, desquamating agents, keratolytic agents, antimicrobial agents, antifungal agents, fungistatic agents, bactericidal agents, bacteriostatic agents, antihyperkeratosis agents, comedolytic agents, anti-psoriasis agents, anti-dermatitis agents, anti-eczema agents, DNA repairing agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, cosmetic deodorant agent and/or body odor absorbent agent and/or body odor masking agent and/or antiperspirant agent, scented substance and/or scented oil, agents stimulating healing, coadjuvant healing agents, agents stimulating reepithelialization, coadjuvant reepithelialization agents, cytokine growth factors, calming agents, anti-inflammatory agents and/or analgesics, anesthetic agents, PAR-2 activity inhibiting agents, agents acting on capillary circulation and/or microcirculation, agents stimulating angiogenesis, agents inhibiting vascular permeability, venotonic agents, agents acting on cell metabolism, agents to improve dermal-epidermal junction, agents inducing hair growth, hair growth inhibiting or retardant agents, perfumes, chelating agents, plant extracts, essential oils, marine extracts, agents obtained from a biofermentation process, mineral salts, cell extracts, sunscreens and organic or mineral photoprotective agents active against ultraviolet A and/or B rays, and mixtures thereof.

* * * * *